US006071715A

United States Patent [19]
Qian et al.

[11] Patent Number: 6,071,715
[45] Date of Patent: Jun. 6, 2000

[54] NUCLEIC ACIDS ENCODING NOVEL PROTEINS WHICH BIND TO RETINOBLASTOMA PROTEIN

[75] Inventors: Yue-Wei Qian; Eva Y. H. P. Lee, both of San Antonio, Tex.

[73] Assignee: Board of Regents, The University of Texas System, Austin, Tex.

[21] Appl. No.: 08/105,454

[22] Filed: Aug. 12, 1993

[51] Int. Cl.$^7$ .................................................. C12H 15/12
[52] U.S. Cl. .................. 435/69.1; 435/252.3; 435/254.2; 435/320.1; 435/325; 536/23.5; 536/24.31
[58] Field of Search ............................... 536/23.5, 24.31; 435/69.1, 240.1, 320.1, 255, 252.33, 254.2, 325

[56] References Cited

PUBLICATIONS

Bandara and La Thangue, "Adenovirus Ela prevents the retinoblastoma gene product from complexing with a cellular transcription factor," *Nature,* 351:494–397, 1991.

DeCaprio et al., "The product of the retinoblastoma susceptibility gene has properties of a cell cycle regulatory element," *Cell,* 58:1085–1095, 1989.

Defeo–Jones et al., "Cloning of cDNAs for cellular proteins that bind to the retinoblastoma gene product," *Nature,* 352:251–254, 1991.

Helin et al., "A cDNA Encoding a pRB–Binding Protein with Properties of the Transcription Factor E1F," *Cell,* 70:337–350, 1992.

Huang et al., "A cellular protein that competes with SV40 T antigen for binding to the retinoblastoma gene product," *Nature,* 350:160–162, 1991.

Ikawa and Weinberg, "An interaction between p21$^{ras}$ and heat shock protein hsp60, a chaperonin," *Proc. Natl. Acad. Sci. USA,* 89:2012–2016, 1992.

Kaelin et al., "Identification of Cellular Proteins that can Interact Specifically with the T/E1A–Binding Region of the Retinoblastoma Gene Product," *Cell,* 64:521–532, 1991.

Kaelin et al., "Expression Cloning of a cDNA Encoding a Retinoblastoma–Binding Protein with E2F–like Properties," *Cell,* 70:351–364, 1992.

Lee et al., "RB Protein as a Cellular "Corral" for Growth––promoting Proteins," *Cold Spring Harbor Symposia on Quantitative Biology,* LVI:211–217, 1991.

McCormick, "How receptors turn Ras on," *Nature,* 363:15–16, 1993.

Nihei et al., "Protein Interaction of Retinoblastoma Gene Product pRb110 with $M_r$ 73,000 Heat Shock Cognate Protein," *Cancer Research,* 53:1702–1705, 1993.

Ruggieri et al., MSI1, a negative regulator of the RAS––cAMP pathway in *Saccharomyces cerevisiae, Proc. Natl. Acad. Sci. USA,* 86:8778–8782, 1989.

Shan et al., "Molecular Cloning of Cellular Genes Encoding Retinoblastoma–Associated Proteins: Identification of a Gene with Properties of the Transcription factor E2F," *Molecular and Cellular Biology,* 12(12):5620–5631, 1992.

Whyte et al., "Association between an oncogene and an anti–oncogene: the adenovirus E1A proteins bind to the retinoblastoma gene product," *Nature,* 334:124–129, 1988.

*Primary Examiner*—Sally Teng
*Attorney, Agent, or Firm*—Arnold White & Durkee

[57] ABSTRACT

The retinoblastoma protein (Rb) is the product of the retinoblastoma gene and has been found to contain mutations in retinoblastoma tumor cells. Two nuclear proteins that bind to Rb, p48 and p46 have been isolated and the genes have been cloned. These proteins bind to Rb competitively with the SV40 T antigen. p48 is shown to suppress heat shock sensitive Ras mutations in yeast and is implicated as a modulator of the retinoblastoma suppressor function of Rb.

44 Claims, 11 Drawing Sheets

```
                                       CGCGCGCACAGAGCGAGCTCTTGC   24
AGCCTCCCCGCCCCTCCCGCAACGCTCGACCCCAGGATTCCCCCGGCTCGCCTGCCCGCCATG   87
                                                               M   1

GCCGACAAGGAAGCAGCCTTCGACGACGCAGTGGAAGAACGAGTGATCAACGAGGAATACAAA  150
 A  D  K  E  A  A  F  D  D  A  V  E  E  R  V  I  N  E  E  Y  K   22

ATATGGAAAAAGAACACCCCTTTTCTTTATGATTTGGTGATGACCCATGCTCTGGAGTGGCCC  213
 I  W  K  K  N  T  P  F  L  Y  D  L  V  M  T  H  A  L  E  W  P   43

AGCCTAACTGCCCAGTGGCTTCCAGATGTAACCAGACCAGAAGGGAAAGATTTCAGCATTCAT  276
 S  L  T  A  Q  W  L  P  D  V  T  R  P  E  G  K  D  F  S  I  H   64

CGACTTGTCCTGGGGACACACACATCGGATGAACAAAACCATCTTGTTATAGCCAGTGTGCAG  339
 R  L  V  L  G  T  H  T  S  D  E  Q  N  H  L  V  I  A  S  V  Q   85

CTCCCTAATGATGATGCTCAGTTTGATGCGTCACACTACGACAGTGAGAAAGGAGAATTTGGA  402
 L  P  N  D  D  A  Q  F  D  A  S  H  Y  D  S  E  K  G  E  F  G  106

GGTTTTGGTTCAGTTAGTGGAAAAATTGAAATAGAAATCAAGATCAACCATGAAGGAGAAGTA  465
 G  F  G  S  V  S  G  K  I  E  I  E  I  K  I  N  H  E  G  E  V  127

AACAGGGCCCGTTATATGCCCCAGAACCCTTGTATCATCGCAACAAAGACTCCTTCCAGTGAT  528
 N  R  A  R  Y  M  P  Q  N  P  C  I  I  A  T  K  T  P  S  S  D  148

GTTCTTGTCTTTGACTATACAAAACATCCTTCTAAACCAGATCCTTCTGGAGAGTGCAACCCA  591
 V  L  V  F  D  Y  T  K  H  P  S  K  P  D  P  S  G  E  C  N  P  169

GACTTGCGTCTCCGTGGACATCAGAAGGAAGGCTATGGGCTTTCTTGGAACCCAAATCTCAGT  654
 D  L  R  L  R  G  H  Q  K  E  G  Y  G  L  S  W  N  P  N  L  S  190

GGGCACTTACTTAGTGCTTCAGATGACCATACCATCTGCCTGTGGGACATCAGTGCCGTTCCA  717
 G  H  L  L  S  A  S  D  D  H  T  I  C  L  W  D  I  S  A  V  P  211

AAGGAGGGAAAAGTGGTAGATGCGAAGACCATCTTTACAGGGCATACGGCAGTAGTAGAAGAT  780
 K  E  G  K  V  V  D  A  K  T  I  F  T  G  H  T  A  V  V  E  D  232

GTTTCCTGGCATCTACTCCATGAGTCTCTGTTTGGGTCAGTTGCTGATGATCAGAAACTTATG  843
 V  S  W  H  L  L  H  E  S  L  F  G  S  V  A  D  D  Q  K  L  M  253
```

FIG. 1B-1

```
ATTTGGGATACTCGTTCAAACAATACTTCCAAACCAAGCCACTCAGTTGATGCTCACACTGCT    906
 I  W  D  T  R  S  N  N  T  S  K  P  S  H  S  V  D  A  H  T  A    274

GAAGTGAACTGCCTTTCTTTCAATCCTTATAGTGAGTTCATTCTTGCCACAGGATCAGCTGAC    969
 E  V  N  C  L  S  F  N  P  Y  S  E  F  I  L  A  T  G  S  A  D    295

AAGACTGTTGCCTTGTGGGATCTGAGAAATCTGAAACTTAAGTTGCATTCCTTTGAGTCACAT   1032
 K  T  V  A  L  W  D  L  R  N  L  K  L  K  L  H  S  F  E  S  H    316

AAGGATGAAATATTCCAGGTTCAGTGGTCACCTCACAATGAGACTATTTTAGCTTCCAGTGGT   1095
 K  D  E  I  F  Q  V  Q  W  S  P  H  N  E  T  I  L  A  S  S  G    337

ACTGATCGCAGACTGAATGTCTGGGATTTAAGTAAAATTGGAGAGGAACAATCCCCAGAAGAT   1158
 T  D  R  R  L  N  V  W  D  L  S  K  I  G  E  E  Q  S  P  E  D    358

GCAGAAGACGGGCCACCAGAGTTGTTGTTTATTCATGGTGGTCATACTGCCAAGATATCTGAT   1221
 A  E  D  G  P  P  E  L  L  F  I  H  G  G  H  T  A  K  I  S  D    379

TTCTCCTGGAATCCCAATGAACCTTGGGTGATTTGTTCTGTATCAGAAGACAATATCATGCAA   1284
 F  S  W  N  P  N  E  P  W  V  I  C  S  V  S  E  D  N  I  M  Q    400

GTGTGGCAAATGGCAGAGAACATTTATAATGATGAAGACCCTGAAGGAAGCGTGGATCCAGAA   1347
 V  W  Q  M  A  E  N  I  Y  N  D  E  D  P  E  G  S  V  D  P  E    421

GGACAAGGGTCCTAGATATGTCTTTACTTGTTGTGATTTTAGACTCCCCTTTTTTCTTCTCAA   1410
 G  Q  G  S  (SEQ ID NO:2)                                         425

CCCTGAGAGTGATTTAACACTGGTTTTGAGACAGACTTTATTCAGCTATCCCTCTATATAATA   1473

GGTACCACCGATAATGCTATTAGCCCAAACCGTGGGTTTTTCTAAATATTAATAGGGGGGCTT   1536

GATTCAACAAAGCCACAGACTTAACGTTGAAATTTTCTTCAGGAATTTTCTAGTAACCCAGGT   1599

CTAAAGTAGCTACAGAAAGGGGAATATTATGTGTGATTATTTTTCTTCTTATGCTATATCCCC   1662
```

FIG. 1B-2

```
AAGTTTTTCAGACTCATTTAAGTAAAGGCTAGAGTGAGTAAGGAATAGAGCCAAATGAGGTAG    1725

GTGTCTGAGCCATGAAGTATAAATACTGAAAGATGTCACTTTTATTCAGGAAATAGGGGGAGT    1788

TCAAGTCGTATAGATTCCTACTCGAAAATCTTGACACCTGACTTTCCAGGATGCACATTTTCA    1851

TACGTAGACCAGTTTCCTCTTGGTTTCTTCAGTTAAGTCAAAACAACACGTTCCTCTTTCCCC    1914

ATATATTCATATATTTTTGCTCGTTAGTGTATTTCTTGAGCTGTTTTCATGTTGTTTATTTCC    1977

TGTCTGTGAAATGGTGTTTTTTTTTTTGTTGTTGGTTTTTTTTTTTTTTTTTAACTTGGGAC     2040

CACCAAGTTGTAAAGATGTATGTTTTTACCTGACAGTTATACCACAGGTAGACTGTCAAGTTG    2103

AGAAGAGTGAATCAATAACTTGTATTTGTTTTAAAAATTAAATTAATCCTTGATAAGAGTTGC    2166

TTTTTTTTTTTAGGAGTTAGTCCTTGACCACTAGTTTGATGCCATCTCCATTTTGGGTGACCT    2229

GTTTCACCAGCAGGCCTGTTACTCTCCATGACTAACTGTGTAAGTGCTTAAAATGGAATAAAT    2292

TGCTTTTCTACATAAAAAAAAA (SEQ ID NO:1)                               2314
```

FIG. 1B-3

```
GGAGGCGCGGGTTGAAAAGTCTCGTTCCAAGTTTGGAGAGAG          42

AGAGAAGAGCGCCTCAGACCTCGGTACCCGCGAGCGGGGAGGACCCAGGAAAGAAGGACGCGGCGT    108

CTGGGGAGCACCCAGGCAGCAAGACGGGGCCCGGGCTTTCGACAGTGGGGAGTGTGACGCGCTTGG    174

GAAAGGCAGGAGCGCCAGCGGTCGGGCTGCTCTTGGCTAACGAGAGGAGTCCGAGGCGGCGGCGAG    240

GGGCGAACGACCCGACGCAAGATGGCGAGTAAAGAGATGTTTGAAGATACTGTGGAGGAGCGTGTC    306
                    M   A   S   K   E   M   F   E   D   T   V   E   E   R   V    15
ATCAATGAAGAATATAAAATCTGGAAGAAGAATACACCGTTTCTATATGACCTGGTTATGACCCAT    372
 I   N   E   E   Y   K   I   W   K   K   N   T   P   F   L   Y   D   L   V   M   T   H    37
GCTCTTCAGTGGCCCAGTCTTACCGTTCAGTGGCTTCCTGAAGTGACTAAACCTGAAGGAAAAGAT    438
 A   L   Q   W   P   S   L   T   V   Q   W   L   P   E   V   T   K   P   E   Q   K   D    55
TATGCCCTTCATTGGCTAGTGCTGGGGACTCATACGTCTGATGAGCAGAATCATCTGGTGGTTGCT    504
 Y   A   L   M   W   L   V   L   G   T   H   T   S   D   E   Q   N   H   L   V   V   A    74
CGAGTACATATTCCCAATGATGATGCACAGTTTGATGCTTCCCATTGTGACAGTGACAAGGGTGAA    570
 R   V   H   I   P   N   D   D   A   Q   F   D   A   S   H   C   D   S   D   K   G   E    96
TTTGGTGGCTTTGGTTCTGTAACAGGAAAAATTGAATGTGAAATTAAAATCAATCACGAAGGAGAA    636
 F   G   G   F   G   S   V   T   G   K   I   E   C   E   I   K   I   N   H   E   G   E    118
GTAAACCGTGCTCGTTACATGCCGCAGAATCCTCACATCATTGCTACAAAAACACCATCTTCTGAT    702
 V   N   R   A   R   T   M   P   Q   N   P   H   I   I   A   T   K   T   P   S   S   D    140
GTGTTGGTTTTTGACTATACAAAACACCCTGCTAAACCAGACCCAAGTGGAGAATGTAATCCTGAT    768
 V   L   V   F   D   Y   T   K   H   P   A   K   P   D   P   S   G   E   C   N   P   D    162
CTCAGATTAAGAGGTCACCAGAAGGAAGGCTATGGTCTCTCCTGGAATTCAAATTTGAGTGGACAT    834
 L   R   L   R   G   H   Q   K   E   G   Y   G   L   S   W   N   S   N   L   S   G   H    184
CTCCTAAGTGCATCTGATGACCATACTGTTTGTCTGTGGGATATAAACGCAGGACCAAAAGAAGGC    900
 H   L   L   S   A   S   D   D   H   T   V   C   L   W   D   I   N   A   Q   P   K   E    206
AAAATTGTGGATGCTAAAGCCATCTTTACTGGCCACTCAGCTGTTGTAGAGGATGTGGCCTGGCAC    966
 G   K   I   V   D   A   K   A   I   F   T   G   H   S   A   V   V   E   D   V   A   W    228
CTGCTGCACGAGTCATTGTTTGGATCTGTTGCTGATGATCAGAAACTTATGATATGGGACACCAGG    1032
 H   L   L   H   E   S   L   F   G   S   V   A   D   D   Q   K   L   M   I   W   D   T    250
TCCAATACCACCTCCAAGCCGAGTCACTTGGTGGATGCGCACACTGCCGAAGTCAACTGCCTCTCA    1098
 R   S   N   T   T   S   K   P   S   H   L   V   D   A   H   T   A   E   V   N   C   L    272
TTCAATCCCTACAGCGAATTTATTCTAGCCACCGGCTCTGCGGATAAGACCGTAGCTTTATGGGAT    1164
 S   F   N   P   Y   S   E   F   I   L   A   T   G   S   A   D   K   T   V   A   L   W    294
CTGCGTAACTTAAAATTAAAACTCCATACCTTCGAATCTCATAAAGATGAAATTTTCCAGGTCCAC    1230
 D   L   R   N   L   K   L   K   L   H   T   F   E   S   H   K   D   E   I   F   Q   V    316
TGGTCTCCACATAATGAAACTATTCTGGCTTCAAGTGGTACTGACCGCCGCCTGAATGTGTGGGAT    1296
```

FIG. 5A

```
  H   W   S   P   H   N   E   T   I   L   A   S   S   G   T   D   R   R   L   N   V   W        338
ATTCATGGAGGACACACTGCTAAGATTTCAGATTTTAGCTGGAACCCCAATGAGCCTTGGGTCATT                              1362
  D   L   S   K   I   G   E   E   Q   S   A   E   D   A   E   D   G   P   P   E   L   L        360
TGCTCAGTGTCTGAGGATAACATCATGCAGATATGGCAAATGGCTGAAAATATTTACAATGATGAA                             1428
  F   I   H   G   G   H   T   A   K   I   S   D   F   S   W   N   P   N   E   P   W   V        382
GAGTCAGATGTCACGACATCCGAACTGGAGGGACAAGGATCTTAAACCCAAAGTACGAGAAATGTT                             1494
  I   C   S   V   S   E   D   N   I   M   Q   I   W   Q   M   A   E   N   I   Y   N   D        404
TCTGTTGAATGTAATGCTACATGAATGCTTGATTTATCAAGCGCCAAAAAGGCATTGTATAGTAGG                             1560
  E   E   S   D   V   T   T   S   E   L   E   G   Q   G   S                                    419
AAATGTAAGTGGGGTGGCTTATGGCTTCTTTATCCTCTGATTCTAGCACTTTCAAGTGAGCTGTTG                             1626
CGTACTGTATCATATTGTAGCTATTAGGGAAGAGAAGAATGTTGCTTAAGAAAGAACATCACCATT                             1692
GATTTTAAATACAACTAGCAGGGTATTGCCTTTGATTCAACTGTTTTAAGTCCTCATTTTCTCAAA                             1758
CTAAGTGCTTGCTGTTCCCAAATATGCAAGAATAACTTTTACACTTTTTCCTTCCAACACTTCTTG                             1824
ATTGGCTTTGCAGAAATAAAGTTTTAAAATAAAAAAAAA (SEQ ID NO:9)                                          1863
```

FIG. 5B

MASKEMFEDT VEERVINEEY KIWKKNTPFL YDLVMTHALQ WPSLTVQWLP EVTKPEQKDY  60
ALHWLVLGTH TSDEQNHLVV ARVHIPNDDA QFDASHCDSD KGEFGGFGSV TGKIECEIKI 120
NHEGEVNRAR YMPQNPHIIA TKTPSSDVLV FDYTKHPAKP DPSGECNPDL RLRGHQKEGY 180
GLSWNSNLSG HLLSASDDHT VCLWDINAQP KEGKIVDAKA IFTGHSAVVE DVAWHLLHES 240
LFGSVADDQK LMIWDTRSNT TSKPSHLVDA HTAEVNCLSF NYPSEFILAT GSADKTVALW 300
DLRNLKLKLH TFESHKDEIF QVHWSPHNET ILASSGTDRR LNVWDLSKIG EEQSAEDAED 360
GPPELLFIHG GHTAKISDFS WNPNEPWVIC SVSEDNIMQI WQMAENIYND EESDVTTSEL 420
EGQGS (SEQ ID NO:10)                                             425

FIG. 6

P48-PROTEIN(SEQ ID NO: 2) MADKEAAFDDAVEERVINEEYKIWKKNTPFLYDLVMTHAL    40
P46-PROTEIN(SEQ ID NO:10) MASKEMFEDTVEERVINEEYKIWKKNTPFLYDLVMTHALQ    40

EWPSLTAQWLPDVTRPEGKDFSIHRLVLGTHTSDEQNHLYMASVQLPNDDAQFDASHYDSEKGEFG      106
WPSLTVQWLPEVTKPEQKDYALHWLVLGTHTSDEQNHLVVARVHIPNDDAQFDASHCDSDKGEFGGF    107

GFGSVSGKIEIEIKINHEGEVNRARYMPQNPCIIATKTPSSDVLVFDYTKHPSKPDPSGECNPDLRL    173
GSVTGKIECEIKINHEGEVNRARYMPQNPHIIATKTPSSDVLVFDYTKHPAKPDPSGECNPDLRLRG    174

RGHQKEGYGLSWNPNLSGHLLSASDDHTICLWDISAVPKEGKVVDAKTIFTGHTAVVEDVSWHLLHES   241
HQKEGYGLSWNSNLSGHLLSASDDHTVCLWDINAQPKEGKIVDAKAIFTGHSAVVEDVAWHLLHESLF   242

LFGSVADDQKLMIWDTRSNNTSKPSHSVDAHTAEVNCLSFNPYSEFILATGSADKTVALWDLRNLKLKL  310
GSVADDQKLMIWDTRSNTTSKPSHLVDAHTAEVNCLSFNPYSEFILATGSADKTVALWDLRNLKLKLHT  311

HSFESHKDEIFQVQWSPHNETILASSGTDRRLNVWDLSKIGEEQSPEDAEDGPPELLFIHGGHTAKISD  379
FESHKDEIFQVHWSPHNETILASSGTDRRLNVWDLSKIGEEQSAEDAEDGPPELLFIHGGHTAKISDFS 380

FSWNPNEPWVICSVSEDNIMQVWQMAENIYNDEDPEGSVDPEGQGS (SEQ ID NO:2)   425
WNPNEPWVICSVSEDNIMQIWQMAENIYNDEESDVTTSELEGQGS  (SEQ ID NO:10)  425

FIG. 7

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 2314 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 85..1362

(xi) SEQUENCE DESCRIPTION: SEQ ID NO:1:

```
CGCGCGCACA GAGCGAGCTC TTGCAGCCTC CCCGCCCCTC CCGCAACGCT CGACCCCAGG   60
ATTCCCCCGG CTCGCCTGCC CGCCATGGCC GACAAGGAAG CAGCCTTCGA CGACGCAGTG  120
GAAGAACGAG TGATCAACGA GGAATACAAA ATATGGAAAA AGAACACCCC TTTTCTTTAT  180
GATTTGGTGA TGACCCATGC TCTGGAGTGG CCCAGCCTAA CTGCCCAGTG GCTTCCAGAT  240
GTAACCAGAC CAGAAGGGAA AGATTTCAGC ATTCATCGAC TTGTCCTGGG GACACACACA  300
TCGGATGAAC AAAACCATCT TGTTATAGCC AGTGTGCAGC TCCCTAATGA TGATGCTCAG  360
TTTGATGCGT CACACTACGA CAGTGAGAAA GGAGAATTTG GAGGTTTTGG TTCAGTTAGT  420
GGAAAAATTG AAATAGAAAT CAAGATCAAC CATGAAGGAG AAGTAAACAG GGCCCGTTAT  480
ATGCCCCAGA ACCCTTGTAT CATCGCAACA AAGACTCCTT CCAGTGATGT TCTTGTCTTT  540
GACTATACAA AACATCCTTC TAAACCAGAT CCTTCTGGAG AGTGCAACCC AGACTTGCGT  600
CTCCGTGGAC ATCAGAAGGA AGGCTATGGG CTTTCTTGGA ACCCAAATCT CAGTGGGCAC  660
TTACTTAGTG CTTCAGATGA CCATACCATC TGCCTGTGGG ACATCAGTGC CGTTCCAAAG  720
GAGGGAAAAG TGGTAGATGC GAAGACCATC TTTACAGGGC ATACGGCAGT AGTAGAAGAT  780
GTTTCCTGGC ATCTACTCCA TGAGTCTCTG TTTGGGTCAG TTGCTGATGA TCAGAAACTT  840
ATGATTTGGG ATACTCGTTC AAACAATACT TCCAAACCAA GCCACTCAGT TGATGCTCAC  900
ACTGCTGAAG TGAACTGCCT TTCTTTCAAT CCTTATAGTG AGTTCATTCT TGCCACAGGA  960
TCAGCTGACA AGACTGTTGC CTTGTGGGAT CTGAGAAATC TGAAACTTAA GTTGCATTCC 1020
TTTGAGTCAC ATAAGGATGA AATATTCCAG GTTCAGTGGT CACCTCACAA TGAGACTATT 1080
TTAGCTTCCA GTGGTACTGA TCGCAGACTG AATGTCTGGG ATTTAAGTAA AATTGGAGAG 1140
GAACAATCCC CAGAAGATGC AGAAGACGGG CCACCAGAGT TGTTGTTTAT TCATGGTGGT 1200
CATACTGCCA AGATATCTGA TTTCTCCTGG AATCCCAATG AACCTTGGGT GATTTGTTCT 1260
GTATCAGAAG ACAATATCAT GCAAGTGTGG CAAATGGCAG AGAACATTTA TAATGATGAA 1320
GACCCTGAAG GAAGCGTGGA TCCAGAAGGA CAAGGGTCCT AGATATGTCT TTACTTGTTG 1380
TGATTTTAGA CTCCCCTTTT TTCTTCTCAA CCCTGAGAGT GATTTAACAC TGGTTTTGAG 1440
ACAGACTTTA TTCAGCTATC CCTCTATATA ATAGGTACCA CCGATAATGC TATTAGCCCA 1500
AACCGTGGGT TTTTCTAAAT ATTAATAGGG GGGCTTGATT CAACAAAGCC ACAGACTTAA 1560
CGTTGAAATT TTCTTCAGGA ATTTTCTAGT AACCCAGGTC TAAAGTAGCT ACAGAAAGGG 1620
```

```
GAATATTATG TGTGATTATT TTTCTTCTTA TGCTATATCC CCAAGTTTTT CAGACTCATT    1680

TAAGTAAAGG CTAGAGTGAG TAAGGAATAG AGCCAAATGA GGTAGGTGTC TGAGCCATGA    1740

AGTATAAATA CTGAAAGATG TCACTTTTAT TCAGGAAATA GGGGGAGTTC AAGTCGTATA    1800

GATTCCTACT CGAAAATCTT GACACCTGAC TTTCCAGGAT GCACATTTTC ATACGTAGAC    1860

CAGTTTCCTC TTGGTTTCTT CAGTTAAGTC AAAACAACAG GTTCCTCTTT CCCCATATAT    1920

TCATATATTT TTGCTCGTTA GTGTATTTCT TGAGCTGTTT TCATGTTGTT TATTTCCTGT    1980

CTGTGAAATG GTGTTTTTTT TTTTGTTGTT GGTTTTTTTT TTTTTTTTTT AACTTGGGAC    2040

CACCAAGTTG TAAAGATGTA TGTTTTTACC TGACAGTTAT ACCACAGGTA GACTGTCAAG    2100

TTGAGAAGAG TGAATCAATA ACTTGTATTT GTTTTAAAAA TTAAATTAAT CCTTGATAAG    2160

AGTTGCTTTT TTTTTTTAGG AGTTAGTCCT TGACCACTAG TTTGATGCCA TCTCCATTTT    2220

GGGTGACCTG TTTCACCAGC AGGCCTGTTA CTCTCCATGA CTAACTGTGT AAGTGCTTAA    2280

AATGGAATAA ATTGCTTTTC TACATAAAAA AAAA                                2314

(2) INFORMATION FOR SEQ ID NO:2:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Asp Lys Glu Ala Ala Phe Asp Asp Ala Val Glu Glu Arg Val
  1               5                  10                  15

Ile Asn Glu Glu Tyr Lys Ile Trp Lys Lys Asn Thr Pro Phe Leu Tyr
                 20                  25                  30

Asp Leu Val Met Thr His Ala Leu Glu Trp Pro Ser Leu Thr Ala Gln
             35                  40                  45

Trp Leu Pro Asp Val Thr Arg Pro Glu Gly Lys Asp Phe Ser Ile His
         50                  55                  60

Arg Leu Val Leu Gly Thr His Thr Ser Asp Glu Gln Asn His Leu Val
 65                  70                  75                  80

Ile Ala Ser Val Gln Leu Pro Asn Asp Asp Ala Gln Phe Asp Ala Ser
                 85                  90                  95

His Tyr Asp Ser Glu Lys Gly Glu Phe Gly Gly Phe Gly Ser Val Ser
                100                 105                 110

Gly Lys Ile Glu Ile Glu Ile Lys Ile Asn His Glu Gly Glu Val Asn
            115                 120                 125

Arg Ala Arg Tyr Met Pro Gln Asn Pro Cys Ile Ile Ala Thr Lys Thr
130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190

Leu Leu Ser Ala Ser Asp Asp His Thr Ile Cys Leu Trp Asp Ile Ser
        195                 200                 205

Ala Val Pro Lys Glu Gly Lys Val Val Asp Ala Lys Thr Ile Phe Thr
    210                 215                 220
```

```
Gly His Thr Ala Val Val Glu Asp Val Ser Trp His Leu Leu His Glu
225                 230                 235                 240

Ser Leu Phe Gly Ser Val Ala Asp Asp Gln Lys Leu Met Ile Trp Asp
            245                 250                 255

Thr Arg Ser Asn Asn Thr Ser Lys Pro Ser His Ser Val Asp Ala His
            260                 265                 270

Thr Ala Glu Val Asn Cys Leu Ser Phe Asn Pro Tyr Ser Glu Phe Ile
        275                 280                 285

Leu Ala Thr Gly Ser Ala Asp Lys Thr Val Ala Leu Trp Asp Leu Arg
        290                 295                 300

Asn Leu Lys Leu Lys Leu His Ser Phe Glu Ser His Lys Asp Glu Ile
305                 310                 315                 320

Phe Gln Val Gln Trp Ser Pro His Asn Glu Thr Ile Leu Ala Ser Ser
                325                 330                 335

Gly Thr Asp Arg Arg Leu Asn Val Trp Asp Leu Ser Lys Ile Gly Glu
                340                 345                 350

Glu Gln Ser Pro Glu Asp Ala Glu Asp Gly Pro Pro Glu Leu Leu Phe
            355                 360                 365

Ile His Gly Gly His Thr Ala Lys Ile Ser Asp Phe Ser Trp Asn Pro
370                 375                 380

Asn Glu Pro Trp Val Ile Cys Ser Val Ser Glu Asp Asn Ile Met Gln
385                 390                 395                 400

Val Trp Gln Met Ala Glu Asn Ile Tyr Asn Asp Glu Asp Pro Glu Gly
                405                 410                 415

Ser Val Asp Pro Glu Gly Gln Gly Ser
            420                 425
```

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Glu Asn Leu Phe Cys Ser Glu Glu Met Pro Ser Ser Asp Asp Glu Ala
  1               5                  10                  15

Ala Thr
```

(2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Glu Asn Leu Phe Cys Ser Lys Glu Met Pro Ser Ser Asp Asp Glu Ala
  1               5                  10                  15

Ala Thr
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Glu Gly Gln Gly Ser
 1               5

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Ala Ala Asn Lys Ala Arg Lys Glu Ala Glu Leu Ala Ala Ala Asn Ala
 1               5                  10                  15

Glu Gln (2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: R
        (B) LOCATION: 3, 15, and 18
        (C) IDENTIFICATION METHOD: R = A or G (ix) FEATURE:
        (A) NAME/KEY: Y
        (B) LOCATION: 6
        (C) IDENTIFICATION METHOD: Y = C or T (ix) FEATURE:
        (A) NAME/KEY: H
        (B) LOCATION: 9
        (C) IDENTIFICATION METHOD: H = A or C or T (ix) FEATURE:
        (A) NAME/KEY: B
        (B) LOCATION: 12
        (C) IDENTIFICATION METHOD: B = G or T or C (ix) FEATURE:
        (A) NAME/KEY: M
        (B) LOCATION: 19
        (C) IDENTIFICATION METHOD: M = A or C (xi) SEQUENCE DESCRIPTION: SEQ ID NO:7:

GARGAYACHG TBGARGARMG                                         20

(2) INFORMATION FOR SEQ ID NO:8:

(i) SEQUENCE CHARACTERISTICS:
        (A) LENGTH: 23 base pairs
        (B) TYPE: nucleic acid (C) STRANDEDNESS: single
        (D) TOPOLOGY: linear (ii) MOLECULE TYPE: DNA (ix) FEATURE:
        (A) NAME/KEY: R
        (B) LOCATION: 3, 15 and 21
        (C) IDENTIFICATION METHOD:  R  =  A or G (ix) FEATURE:
        (A) NAME/KEY: Y
        (B) LOCATION: 6, 9 and 18
        (C) IDENTIFICATION METHOD:  Y =  C or T (xi) SEQUENCE DESCRIPTION: SEQ ID NO:8:

GTRTTYTTYT TCCARATYTT RTA                                               23

(2) INFORMATION FOR SEQ ID NO:9:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GGAGGCGCGG GTTGAAAAGT CTCGTTCCAA GTTTGGAGAG AGAGAGAAGA GCGCCTCAGA    60

CCTCGGTACC CGCGAGCGGG GAGGACCCAG GAAAGAAGGA CGCGGCGTCT GGGGAGCACC   120

CAGGCAGCAA GACGGGGCCC GGGCTTTCGA CAGTGGGGAG TGTGACGCGC TTGGGAAAGG   180

CAGGAGCGCC AGCGGTCGGG CTGCTCTTGG CTAACGAGAG GAGTCCGAGG CGGCGGCGAG   240

GGGCGAACGA CCCGACGCAA GATGGCGAGT AAAGAGATGT TGAAGATAC TGTGGAGGAG   300

CGTGTCATCA ATGAAGAATA TAAAATCTGG AAGAAGAATA CACCGTTTCT ATATGACCTG   360

GTTATGACCC ATGCTCTTCA GTGGCCCAGT CTTACCGTTC AGTGGCTTCC TGAAGTGACT   420

AAACCTGAAG GAAAAGATTA TGCCCTTCAT TGGCTAGTGC TGGGGACTCA TACGTCTGAT   480

GAGCAGAATC ATCTGGTGGT TGCTCGAGTA CATATTCCCA ATGATGATGC ACAGTTTGAT   540

GCTTCCCATT GTGACAGTGA CAAGGGTGAA TTTGGTGGCT TTGGTTCTGT AACAGGAAAA   600

ATTGAATGTG AAATTAAAAT CAATCACGAA GGAGAAGTAA ACCGTGCTCG TTACATGCCG   660

CAGAATCCTC ACATCATTGC TACAAAAACA CCATCTTCTG ATGTGTTGGT TTTTGACTAT   720

ACAAAACACC CTGCTAAACC AGACCCAAGT GGAGAATGTA ATCCTGATCT CAGATTAAGA   780

GGTCACCAGA AGGAAGGCTA TGGTCTCTCC TGGAATTCAA ATTTGAGTGG ACATCTCCTA   840

AGTGCATCTG ATGACCATAC TGTTTGTCTG TGGGATATAA ACGCAGGACC AAAAGAAGGC   900

AAAATTGTGG ATGCTAAAGC CATCTTTACT GGCCACTCAG CTGTTGTAGA GGATGTGGCC   960

TGGCACCTGC TGCACGAGTC ATTGTTTGGA TCTGTTGCTG ATGATCAGAA ACTTATGATA  1020

TGGGACACCA GGTCCAATAC CACCTCCAAG CCGAGTCACT TGGTGGATGC GCACACTGCC  1080

GAAGTCAACT GCCTCTCATT CAATCCCTAC AGCGAATTTA TTCTAGCCAC CGGCTCTGCG  1140

GATAAGACCG TAGCTTTATG GGATCTGCGT AACTTAAAAT TAAAACTCCA TACCTTCGAA  1200

TCTCATAAAG ATGAAATTTT CCAGGTCCAC TGGTCTCCAC ATAATGAAAC TATTCTGGCT  1260

TCAAGTGGTA CTGACCGCCG CCTGAATGTG TGGGATTTAA GTAAAATTGG GGAAGAACAA  1320

TCAGCAGAAG ATGCAGAAGA TGGGCCTCCA GAACTCCTGT TTATTCATGG AGGACACACT  1380

-continued

```
GCTAAGATTT CAGATTTTAG CTGGAACCCC AATGAGCCTT GGGTCATTTG CTCAGTGTCT   1440

GAGGATAACA TCATGCAGAT ATGGCAAATG GCTGAAAATA TTTACAATGA TGAAGAGTCA   1500

GATGTCACGA CATCCGAACT GGAGGGACAA GGATCTTAAA CCCAAAGTAC GAGAAATGTT   1560

TCTGTTGAAT GTAATGCTAC ATGAATGCTT GATTTATCAA GCGCCAAAAA GGCATTGTAT   1620

AGTAGGAAAT GTAAGTGGGG TGGCTTATGG CTTCTTTATC CTCTGATTCT AGCACTTTCA   1680

AGTGAGCTGT TGCGTACTGT ATCATATTGT AGCTATTAGG GAAGAGAAGA ATGTTGCTTA   1740

AGAAAGAACA TCACCATTGA TTTTAAATAC AACTAGCAGG GTATTGCCTT TGATTCAACT   1800

GTTTTAAGTC CTCATTTTCT CAAACTAAGT GCTTGCTGTT CCCAAATATG CAAGAATAAC   1860

TTTTACACTT TTTCCTTCCA ACACTTCTTG ATTGGCTTTG CAGAAATAAA GTTTTAAAAT   1920

AAAAAAAAA                                                         1929
```

(2) INFORMATION FOR SEQ ID NO:10:

(i) SEQUENCE CHARACTERISTICS:
        (A) LENGTH: 425 amino acid residues
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Ala Ser Lys Glu Met Phe Glu Asp Thr Val Glu Arg Val Ile
 1               5                  10                  15

Asn Glu Glu Tyr Lys Ile Trp Lys Lys Asn Thr Pro Phe Leu Tyr Asp
            20                  25                  30

Leu Val Met Thr His Ala Leu Gln Trp Pro Ser Leu Thr Val Gln Trp
        35                  40                  45

Leu Pro Glu Val Thr Lys Pro Glu Gln Lys Asp Tyr Ala Leu His Trp
    50                  55                  60

Leu Val Leu Gly Thr His Thr Ser Asp Glu Gln Asn His Leu Val Val
65                  70                  75                  80

Ala Arg Val His Ile Pro Asn Asp Asp Ala Gln Phe Asp Ala Ser His
                85                  90                  95

Cys Asp Ser Asp Lys Gly Glu Phe Gly Gly Phe Gly Ser Val Thr Gly
            100                 105                 110

Lys Ile Glu Cys Glu Ile Lys Ile Asn His Glu Gly Glu Val Asn Arg
        115                 120                 125

Ala Arg Tyr Met Pro Gln Asn Pro His Ile Ile Ala Thr Lys Thr Pro
    130                 135                 140

Ser Ser Asp Val Leu Val Phe Asp Tyr Thr Lys His Pro Ala Lys Pro
145                 150                 155                 160

Asp Pro Ser Gly Glu Cys Asn Pro Asp Leu Arg Leu Arg Gly His Gln
                165                 170                 175

Lys Glu Gly Tyr Gly Leu Ser Trp Asn Ser Asn Leu Ser Gly His Leu
            180                 185                 190

Leu Ser Ala Ser Asp Asp His Thr Val Cys Leu Trp Asp Ile Asn Ala
        195                 200                 205

Gln Pro Lys Glu Gly Lys Ile Val Asp Ala Lys Ala Ile Phe Thr Gly
    210                 215                 220

His Ser Ala Val Val Glu Asp Val Ala Trp His Leu Leu His Glu Ser
225                 230                 235                 240
```

-continued

```
Leu Phe Gly Ser Val Ala Asp Asp Gln Lys Leu Met Ile Trp Asp Thr
            245                 250                 255

Arg Ser Asn Thr Thr Ser Lys Pro Ser His Leu Val Asp Ala His Thr
            260                 265                 270

Ala Glu Val Asn Cys Leu Ser Phe Asn Pro Tyr Ser Glu Phe Ile Leu
        275                 280                 285

Ala Thr Gly Ser Ala Asp Lys Thr Val Ala Leu Trp Asp Leu Arg Asn
        290                 295                 300

Leu Lys Leu Lys Leu His Thr Phe Glu Ser His Lys Asp Glu Ile Phe
305                 310                 315                 320

Gln Val His Trp Ser Pro His Asn Glu Thr Ile Leu Ala Ser Ser Gly
                325                 330                 335

Thr Asp Arg Arg Leu Asn Val Trp Asp Leu Ser Lys Ile Gly Glu Glu
            340                 345                 350

Gln Ser Ala Glu Asp Ala Glu Asp Gly Pro Pro Glu Leu Leu Phe Ile
            355                 360                 365

His Gly Gly His Thr Ala Lys Ile Ser Asp Phe Ser Trp Asn Pro Asn
        370                 375                 380

Glu Pro Trp Val Ile Cys Ser Val Ser Glu Asp Asn Ile Met Gln Ile
385                 390                 395                 400

Trp Gln Met Ala Glu Asn Ile Tyr Asn Asp Glu Glu Ser Asp Val Thr
                405                 410                 415

Thr Ser Glu Leu Glu Gly Gln Gly Ser
            420                 425
```

NUCLEIC ACIDS ENCODING NOVEL PROTEINS WHICH BIND TO RETINOBLASTOMA PROTEIN

The government owns rights in the present invention pursuant to grant number CA49649 from the National Institutes of Health.

BACKGROUND OF THE INVENTION

1. Field of the Invention

The present invention relates generally to the field of cellular regulation. More particularly, it concerns the control of cell growth as affected by the retinoblastoma protein, the implications of this control in cancers including retinoblastoma, and the interactions of oncogenes with cell cycle control proteins and other retinoblastoma associated cellular proteins.

2. Description of the Related Art

Retinoblastoma is a malignant cancer of the developing retina that manifests itself as an intraocular tumor in early childhood (Shields, J. A., 1983). Retinoblastoma occurs in two distinct forms (Vogel, F., 1979). In close to 40% of retinoblastoma cases, tumors appear bilaterally, may be multifocal in each eye, and appear at a very young age. Bilateral retinoblastoma is sometimes diagnosed in newborn infants. In the remaining retinoblastoma cases, tumors are unilateral, are unifocal, and generally present at about 2 years of age.

The pattern of inheritance of retinoblastoma suggests that the wild-type alleles encode a repressor of tumor formation (Migdal, C., 1976). Evidence for the existence of tumor-suppressing genetic factors is also provided by cell fusion studies. Upon fusion of tumor cells with normal fibroblasts, lymphocytes, or keratinocytes (Harris, H., 1986a; Klein, G., et al., 1971), the malignant properties of the original tumor cells are suppressed.

A candidate for the retinoblastoma suppressor gene (Rb) has been cloned, and extensive structural and functional analysis of the gene and its gene product has begun (Goodrich and Lee, 1993). The Rb gene product has properties that suggest a role in regulation of the cell division cycle. For example, Rb protein forms complexes with many cellular and viral proteins, including transcription factors, that influence the cell cycle. The purified Rb protein can also arrest G1 phase progression of the cell cycle when introduced by microinjection. Also, the protein is phosphorylated in a cell cycle dependent manner, suggesting that Rb may be cyclically regulated.

Deletions within the Rb gene have been defined in an extensive number of retinoblastomas (Lee, W.-H., et al., 1987a, 1987b). In addition, about 12–30% of retinoblastomas have detectable genomic rearrangement of Rb, and it is believed that other undetectable small and deletions are present but go unnoticed. In one particular study, a large number of retinoblastoma cell lines and primary tumors were screened and none were detected with normal expression of the Rb protein (Horowitz, J. M., et al., 1990). It is believed that no retinoblastoma primary tumor or cultured cell has been reported to have normal expression of the wild-type Rb gene product. In addition, mutations in the Rb gene have been implicated in other types of cancer such as osteosarcomas, and soft tissue sarcomas (Weichselbaum, R. R., et al., 1988).

An interesting biochemical property of the Rb gene product is its ability to form specific complexes with the transforming proteins of several DNA tumor viruses including SV40 large T, adenovirus E1A, and human papillomavirus E7 (DeCaprio, J. A., et al., 1988; Dyson, N., et al., 1989a; Whyte, P., et al., 1988). The regions of the transforming proteins required for complex formation with Rb are similar to those required for transformation of cells. The amino acids of Rb protein required for binding to SV40 T antigen have also been determined (Huang, S., et al., 1990), and the regions of these amino acids correspond to those frequently mutated in tumor cells. For example, in all cases analyzed to date, mutated Rb proteins from human tumor cells have been unable to form complexes with T antigen. This correlation between the T antigen binding domains and the naturally occurring mutations in cancer cells suggests that these regions constitute an important functional domain.

It is suggested that DNA tumor viruses induce transformation by binding a more active, unphosphorylated form of the Rb protein, thereby inhibiting its normal, suppression function (Ewen, M. E. et al., 1989). The mechanism of transformation by DNA tumor viruses, however, may be more complex than simple inactivation of Rb. Several reports have indicated that binding Rb protein is not sufficient to induce the full transformation potential of some DNA tumor viruses (Manfredi and Prives, 1990; Weber, J. M. et al., 1991). However, binding of DNA tumor virus transforming proteins has pinpointed a region of Rb that is required for protein association and may be important for its normal function.

What is needed, then is a method of regulating cell growth and blocking tumorigenesis through the control of tumor suppressor proteins in their interaction with oncogene products. This control is possible through the interaction of these tumor suppressors and the cellular proteins that bind at functional sites and modulate their biological activity.

SUMMARY OF THE INVENTION

The present invention, in a general and overall sense, concerns novel proteins and polypeptides which bind to the retinoblastoma tumor suppressor protein (Rb), and genes encoding such protein products. More particularly, the invention is directed to isolated and purified DNA segments and recombinant vectors which encode two novel, but related, nuclear proteins termed p48 and p46; to recombinant host cells expressing Rb binding proteins; to compositions containing p48 and p46 proteins and polypeptides, whether natural or recombinant; and to various methods of making and using these DNA segments, cells and proteinaceous compositions.

The retinoblastoma (Rb) gene and gene product are known to act as tumor suppressors, that is, it is known that mutations in Rb correlate with various cancers, typically retinoblastomas, but also osteosarcomas and soft tissue sarcomas. The Rb protein is believed to have many important cellular roles, e.g., in regulating cell division and interacting with transcription factors that influence the cell cycle. Rb protein also interacts with cellular proteins such as transcription factors, oncogenes, structural proteins, signal transducing proteins, kinases, and phosphatases, and viral proteins, including SV40 large T, adenovirus E1A, and human papillomavirus. It is therefore clear that Rb is a very important regulatory protein and, consequently, that any proteins capable of interacting with the carboxyl terminal of Rb protein will affect Rb function to varying extents.

An important embodiment of the present invention is related to the ability of p48 to suppress a Ras mutation. The Ras signal pathway plays a crucial role in neoplasia and in signal transduction in normal cells. For example, it is estimated that Ras mutations occur in 90% of pancreatic tumors. Many other tumors have been found to have mutations in Ras, or in tumor suppressor proteins such as E2F, p53 or Rb. The ability of p48 to bind Rb in a crucial area for the tumor suppressor activity combined with its ability to suppress a Ras mutation phenotype indicate that this protein is an important factor in the tumorigenesis event. It is contemplated that suppression of tumor growth will be possible by decreasing the concentration of p48 in cells by, for example the introduction of antisense RNA complementary to the DNA sequences disclosed in the present invention. Alternatively, p48 levels may be increased by the transfection of tumor cells with the vectors of the present invention.

In an alternate embodiment, the polypeptide and nucleic acid sequences of the present invention will be useful to screen for mutations in the p46 or p48 genes which may be related to the inherited tendency to develop certain types of cancer. The knowledge of whether a patient carries a heterozygous mutation in these important genes will have important implications for gene therapy and genetic counseling.

The ability to screen cell lines for functional mutations in the Rb gene is also an embodiment of the present invention. Since it is known that the viral transforming proteins bind in the same region of Rb as does p48 and p46, these proteins provide a way to screen the lysates of cells to determine whether the Rb protein produced by these cells contains mutations in this important region. Again, this ability to quickly screen for these mutations has valuable implications for gene therapy and for genetic counseling.

In certain embodiments, the invention concerns DNA segments or even genes encoding novel Rb binding proteins. In this respect, the term "gene" is used for simplicity to refer to a functional protein or peptide encoding unit. As will be understood by those in the art, this functional term includes both genomic sequences and cDNA sequences. More particularly, the invention concerns DNA segments encoding the protein termed p48, DNA segments encoding the protein termed p46 and, also, DNA segments encoding peptide or polypeptide fragments of such proteins. As used herein, the term "DNA segment" is intended to refer to a DNA molecule which has been isolated free of total genomic DNA of a particular species, or in particular isolated away from, or purified free from, total genomic DNA of the species from which the DNA is obtained, such as, e.g., mammalian DNA. Included within the term "DNA segment", are DNA segments which may be employed in the preparation of vectors, as well as the vectors themselves, including, for example, plasmids, cosmids, phage, viruses, and the like.

In certain aspects, the invention is directed to DNA segments and recombinant vectors comprising an isolated gene encoding a p48 or p46 protein or polypeptide, and preferably, a p48 or p46 protein which is capable of interacting with retinoblastoma protein (Rb). The p48 protein or polypeptide will include an amino acid sequence in accordance with the amino acid sequence set forth in SEQ ID NO:2, or a portion or biological functional equivalent thereof, whereas the p46 protein or polypeptide will include an amino acid sequence in accordance with the amino acid sequence set forth in SEQ ID NO:10, or a portion or biological functional equivalent thereof.

In other particular embodiments, the invention concerns isolated DNA segments and recombinant vectors which include a nucleic acid sequence in accordance with a continuous segment or segments of the nucleic acid sequences set forth in SEQ ID NO:1 and SEQ ID NO:9. Preferred vectors will generally be those which include, or have, the specific nucleic acid sequence of SEQ ID NO:1 and those which include, or have, the specific nucleic acid sequence of SEQ ID NO:9.

The term "capable of interacting with the retinoblastoma protein" means that upon contacting the retinoblastoma protein, with the p48 or p46 protein, for example, under appropriate conditions of ionic strength, temperature, pH and the like, specific binding will occur. The interaction may occur due to specific electrostatic, hydrophobic, entropic or other interaction of certain amino acid or glycolytic residues of the one protein, Rb, with specific amino acid or glycolytic residues of the second protein, particularly p46 or p48, to form a stable complex under the conditions effective to promote the interaction. The interaction may alter the three dimensional conformation of either or both proteins or polypeptides involved in the interaction and it may also alter the function or activity of either or both proteins or polypeptides involved in the interaction. For example, the interaction of Rb with p48 or p46 may alter the ability of Rb to bind other proteins, such as SV40 T antigen, to bind small molecules, to bind or recognize specific regions of DNA, to act as a substrate for a phosphorylation or dephosphorylation or other enzymatic reaction, or to catalyze or effect any enzymatic reaction involving other substrates and reactants.

In light of the preceding discussion, it will also be understood that the entire length of the Rb, p48 and/or p46 proteins may not be necessary for a specific binding interaction to occur. A smaller polypeptide comprising a portion of the sequence of p48 or p46, such as, for example, a polypeptide of between 300 and about 400 amino acids, or a polypeptide of between 100 and about 200 amino acids, or even polypeptides of between 50 and about 75 amino acids which comprise a portion of the sequence according to SEQ ID NO:2 or SEQ ID NO:10 would be able to interact with Rb and would be encompassed by the present invention. It is also contemplated that smaller polypeptides comprising portions of the amino acid sequence of p46 or p48 of between 20 and about 40 amino acids would be useful in the present invention and that even polypeptides of about 4, 10, or even 15 amino acids which comprise a portion of the sequence according to SEQ ID NO:2 or SEQ ID NO:10 would bind to Rb or would be useful as epitopic core sequences for the production of antibodies to p48 or p46. It is also understood that only a portion of the Rb protein, the carboxy terminal region, for example, may be involved in the interaction.

p48 or p46 protein constructs may also be prepared in which all or a portion of the sequence of SEQ ID NO:2 or seq id no:10 is covalently joined to other amino acid segments, including, but not limited to amino acid segments derived from the sequence of Rb, and amino acid segments which have marker functions or are otherwise detectable. All such fusion polypeptides fall within the scope of the present invention.

Particularly useful recombinant vectors are contemplated to be those vectors, such as plasmids, in which the coding portion of the DNA segment is positioned under the control of a promoter. Such vectors are referred to as "recombinant expression vectors" and they may be generally defined as vectors which are capable of expressing a p48 or p46 protein or polypeptide following their introduction into a host cell, thereby creating a recombinant host cell. Vectors capable of being transformed into, and expressed in, recombinant yeast cells are preferred in certain embodiments. Recombinant plasmids and multicopy plasmids are also preferred, with vectors derived from the plasmid YEp13, for example plasmid YEp24 (New England Biolabs) being particularly preferred.

In expression vectors, the promoter may be in the form of the promoter which is naturally associated with a p48 or p46 gene in mammalian cells. Such a promoter may be obtained by isolating the 5' non-coding sequences located upstream of the coding segment or exon, for example, using recombinant cloning and/or PCR technology in connection with the compositions disclosed herein, particularly the more 5' regions of the p48 and p46 sequences.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a p48 or p46 gene in its natural environment. Such promoters may include promoters normally associated with other mammalian genes, and/or promoters isolated from any other bacterial, viral or eukaryotic gene. Naturally, it will be important to employ a promoter that effectively directs the expression of the DNA segment in the cell type chosen for expression.

Recombinant host cells, including prokaryotic and eukaryotic cells, form another aspect of this invention. In general terms, a recombinant host cell prepared in accordance with the present invention will include a DNA segment or recombinant vector encoding a p48 or p46 protein or polypeptide which includes an amino acid sequence in accordance with SEQ ID NO:2 or SEQ ID NO:10, respectively, or a portion or biological functional equivalent thereof. In preferred embodiments, the DNA segment will be introduced into a cell in the form of a recombinant expression vector, and the resultant recombinant host cell will be capable of expressing recombinant p48 or p46 proteins or polypeptides.

Expression vectors may be employed to express p48 or p46 proteins, polypeptides or peptides in a variety of recombinant host cells, including, by way of example, yeast cells. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant p48 or p46 proteins or peptides. The preferred promoter system contemplated for use in high-level expression includes, but is not limited to ADHI (Berer and Young, 1982).

In connection with expression embodiments to prepare recombinant p48 or p46 proteins and peptides, it is contemplated that longer DNA segments will most often be used, with DNA segments encoding functional domains or the entire p48 or p46 proteins being most preferred. However, it will be appreciated that the use of shorter DNA segments to direct the expression of p48 or p46 peptides or epitopic core regions, such as may be used to generate anti-p48 or anti-p46 antibodies, also falls within the scope of the invention.

In addition to their use in directing the expression of p48 or p46 proteins, the nucleic acid sequences disclosed herein also have a variety of other uses. For example, they also have utility as probes or primers in nucleic acid hybridization embodiments. As such, it is contemplated that oligonucleotide fragments corresponding to the sequence of SEQ ID NO:1 or SEQ ID NO:9 for stretches of between about 10 to 15 nucleotides and about 20 to 30 nucleotides will find particular utility. Longer complementary sequences, e.g., those of about 40, 50, 100, 200, 500, 1000, and even up to full length sequences of about 2291 nucleotides in length for SEQ ID NO:1, and 1668 nucleotides in length for SEQ ID NO:9, will also be of use in certain embodiments.

The ability of such nucleic acid probes to specifically hybridize to p48-encoding or p46-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1 or SEQ ID NO:9 are particularly contemplated as hybridization probes for use in, e.g., Southern and Northern blotting. This would allow p48 or p46 structural or regulatory genes to be analyzed, both in diverse cell types and also in various patients or in other mammalian cells. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, but larger complementary stretches of up to about 2291 (SEQ ID NO:1) or 1668 (SEQ ID NO:9) nucleotides may be used, according to the length complementary sequences one wishes to detect.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1 or SEQ ID NO:9, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

It will also be understood that this invention is not limited to the particular nucleic acid and amino acid sequences of SEQ ID NOS:1, 2, 9 and 10, and the other disclosed herein. Recombinant vectors and isolated DNA segments may therefore variously include p48 or p46 coding regions themselves, coding regions bearing selected alterations or modifications in the basic coding region, or they may encode larger polypeptides which nevertheless include p48-coding or p46-coding regions or may encode biologically functional equivalent proteins or peptides which have variant amino acids sequences.

The DNA segments and proteins of the present invention encompass biologically functional equivalent p48 and p46 proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques. If desired, one may also prepare fusion proteins and peptides, e.g., where the p48 or p46 coding regions are aligned within the same expression unit with other proteins or peptides having desired functions, such as for purification or immunodetection purposes.

In further embodiments, the invention concerns methods for using DNA segments which encode p48 or p46 proteins or polypeptides. One such method of use involves utilizing such novel DNA sequences and segments in processes to prepare compositions which include p48 or p46 proteins or polypeptides, and preferably, substantially purified p48 or p46 proteins or polypeptides. In a general sense, these methods of using DNA include preparing a recombinant vector in which the DNA coding segment is positioned under the control of a promoter and introducing the recombinant vector into a host cell. One would then culture the host cell under conditions effective to allow expression of the encoded p48 or p46 protein or polypeptide, and collect the protein or polypeptide thus expressed.

In preferred embodiments, it is contemplated that one would prepare a recombinant plasmid vector capable of expressing a recombinant p48 or p46 protein, polypeptide or peptide, and introduce the plasmid into a recombinant host cell, most preferably, a yeast cell. One would then produce recombinant p48 or p46 by culturing the recombinant yeast cells under conditions effective to obtain the p48 or p46 protein or polypeptide.

The present invention also encompasses compositions, free from total cellular components, which comprise p48 or p46 protein or polypeptides, and preferably, substantially purified p48 or p46 proteins and polypeptides. Such proteins may either be recombinant p48 or p46, preferably obtained from p48-expressing or p46-expressing recombinant yeast cells. Alternatively, the p48 or p46 may be so-called native or natural p48 or or p46, as isolated and purified from non-recombinant cells, such as human HeLa cells, which express p48 and p46 in the nucleus.

In general, p48 or p46 compositions may be prepared by obtaining an extract from p48-containing or p46-containing cells, whether native or recombinant, subjecting the extract to fractionation and collecting a fraction containing the p48 or p46 protein or polypeptide. In more detail, this includes identifying a positive fraction containing a p48 or p46 protein or polypeptide capable of interacting with the retinoblastoma protein (Rb), and collecting the positive fraction or fractions separately from the other fractions. In this manner, p48 or p46 proteins can be provided essentially free from non-p48 and non-p46 components. A preferred process for extract fractionation is affinity chromatography using a retinoblastoma protein (Rb) affinity column.

In addition to full-length p48 and p46 proteins, such as proteins which have a sequence in accordance with seq id no:2 or SEQ ID NO:10, smaller polypeptides and peptides are also included within the proteinaceous p48 and p46 compositions of present invention. For example, peptides of between about 15 to about 50 amino acids in length, or preferably, of about 15 to about 30 amino acids in length are contemplated.

In still further aspects, the invention concerns anti-p48 and anti-p46 antibody compositions. These include polyclonal and monoclonal antibodies which recognize both the p46 and p48 proteins, although the generation of antibodies which are specific for either the p48 protein or the p46 protein is also contemplated. An antibody prepared in accordance with the present invention may generally be defined as one having binding affinity for a p48 or p46 protein or polypeptide which is capable of interacting with Rb and which include a sequence in accordance with the amino acid sequences set forth in SEQ ID NO:2 or SEQ ID NO:10, or a portion or functional equivalent thereof. The antibodies may be either polyclonal or monoclonal, the latter being exemplified in certain preferred embodiments by the monoclonal antibody termed 13D10 which is disclosed herein.

The p48 and p46 DNA, protein and antibody compositions of the present invention will be useful in a variety of different embodiments. For example, it may be now be determined for the first time whether mutations in p48 or p46 correlate with the presence of tumors in human subjects and patients. This may be done either at the DNA level, using the DNA segments of the invention in any of the nucleic acid hybridization embodiments described herein and known to those of skill in the art, including SSCP (single strand conformation polymorphism) and ribonuclease protection assays which can be used to detect mutations in p48 and/or p46 genes. Equally, diagnostic assays may be conducted at the protein level, e.g., using Western blotting or immunohistochemical analyses. Such techniques may be used to determine whether the protein conformations are changed or whether mutant forms of the proteins exist and correlate with transformed phenotype(s). In addition, it will be significant to discover whether mutations in the p48 or p46 gene may mask or complement mutations in the Rb gene, thereby restoring the tumor suppressing function.

In any event, positive correlations between mutations in p46 or p48, or even in expression levels of either protein and tumorigenesis allow the use of either the nucleic acid segments or polypeptide segments and antibodies thereof of the invention to detect tumor cells, i.e., use as diagnostic or prognostic tools in the detection and monitoring of cancer. The use of the nucleic acid segments, proteins and antibodies thereto of the present invention are also useful to determine if a negative correlation exists. Indeed, if a positive correlation does not exist, it will be of significant value to determine this fact.

The effect of p48 or p46 binding to Rb protein will also have utility in aspects of Rb function other than in its anti-oncogenic capacity. For example, the Rb protein is believed to play a general role in the regulation of cell growth (Lee et al., 1991). This is based on the facts that the phosphorylation state of Rb is cyclic and corresponds to the cell growth cycle, Rb has co-precipitated with the CDC2 complex, and the Rb sequence contains several CDC2 consensus phosphorylation sites. CDC2 is considered to be the principal controller of cell cycle progression in all eukaryotic cells (Draetta, 1990), and thus, is proteins that interact with this complex will have utility in a wide range of biological and medical applications involved in development and growth of organisms and tissues, such as treatment of damaged or atrophied organs, the growth of particular organ tissue for implantation and for wound healing.

A further example of the usefulness of the proteins and peptides of the present invention is embodied in the inventors' discovery that p48 can suppress the heat shock phenotype in a yeast strain carrying a Ras mutation. It is contemplated that p48, and the highly conserved, related protein, p46, can suppress the activity of oncogenic Ras in mammalian cells, and thus that p48 or p46 may be used to suppress the oncogenic p21 Ras in a variety of human tumor types ranging from leukemias to colorectal carcinomas. Pharmaceutical preparations of p48 and p46 compositions formulated in pharmacologically-acceptable vehicles therefore form yet another aspect of the invention.

BRIEF DESCRIPTION OF THE DRAWINGS

FIG. 1 depicts the molecular cloning of RbAp48. FIG. 1 contains parts A–B.

FIG. 1B is the cDNA sequence (SEQ ID NO:1) and the deduced amino acid sequence (SEQ ID NO:2) of RbAp48. The 2,230 nucleotides of the p48 cDNA are shown with the predicted amino acid products (single-letter amino acid code). The numbers correspond to the nucleotide (upper line in each pair) or amino acid (lower line in each pair). An open reading frame of 425 amino acid residues is shown. Arrows indicate the location of the primers used in the PCR reaction. Peptide sequences identical to those obtained from the purified protein are underlined.

FIG. 2 is a demonstration that RbAp48 is a full-length cDNA encoding p48. FIG. 2 contains parts A–C.

FIG. 3 demonstrates the interaction of Rb and p48 in vivo and in vitro. FIG. 3 contains parts A–C.

FIG. 5 is the nucleic acid sequence of the cDNA, RbAp46, and is designated SEQ ID NO:9.

FIG. 6 is the deduced amino acid sequence of the protein, p46, and is designated SEQ ID NO:10

FIG. 7 is the amino acid sequences of p46, SEQ ID NO:2 and p48, SEQ ID NO:10, aligned to illustrate the homology of the two sequences.

DETAILED DESCRIPTION OF THE PREFERRED EMBODIMENTS

The growth suppression function of the retinoblastoma protein (Rb) is thought to be mediated by Rb binding to cellular proteins (Goodrich et al., 1993). The range of proteins that associate with Rb in vitro is quite large and includes transcription factors, oncogenes, structural proteins, possible signal transducing proteins, kinases, and phosphatases (Shan et al., 1992). One of these Rb binding proteins, p48 forms complexes with Rb in vitro and in vivo. This complex formation apparently involves direct interaction between these two ubiquitously expressed nuclear proteins.

Figure 2A:
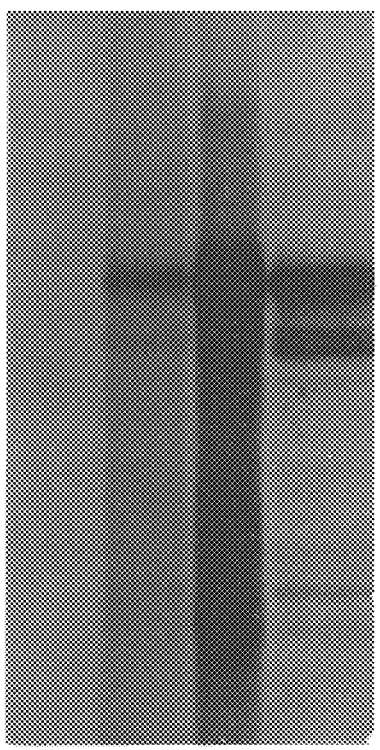
FIG. 2A depicts the products of the in vitro translation of RbAp48 mRNA transcripts. Lane 1 contained no RNA. Transcripts from constructs pGEM-RbAp48 (lane 2) and pb-RbAp48 (containing 5' non-coding sequences of β-globin mRNA, lane 3) were used for in vitro translation. The $^{35}$S-labeled translation products were either directly analyzed by 10% SDS-polyacrylamide gel (lanes 1–3) or analyzed after immunoprecipitation with anti-p48 monoclonal antibody 13D10 (lane 4). The translation efficiency of the chimeric construct containing the 5' untranslated region of the β-globin gene and the coding region of the RbAp48 was found to be 20-fold greater than that of the original RbAp48 clone. This is consistent with a previous report of enhanced translation after the replacement of the 5' untranslated region (Jobling and Gehrke, 1987).
Figure 2B:
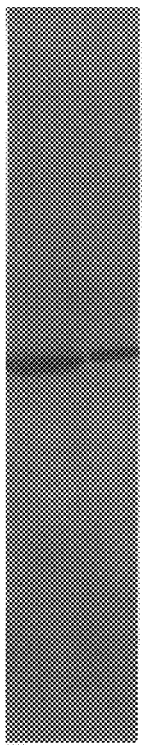
FIG. 2B demonstrates that p48 from the in vitro translation reaction and p48 from the eluate of the Rb-affinity column have similar mobility in an SDS-PAGE analysis. p48 in the eluate (lane 1) or from the in vitro translation reaction (lane 2) were separated by a 10% SDS-PAGE and detected by western blotting with monoclonal antibody 13D10.

An important embodiment of the present invention is the isolation and sequencing of two full-length complementary DNAs, RbAp48 encoding p48 and RbAp46 encoding p46. The two proteins, p48 and p46 share 95% amino acid sequence homology and exhibit crossreactivity with several monoclonal and polyclonal antibodies. It is contemplated, therefore, that the two proteins have similar functions. The 5' and 3' untranslated regions of the RbAp46 clone are significantly different than those regions of the RbAp48 clone, suggesting that these very similar proteins are the products of separate genes. The clones appear to be full-length based on the sequence data and because the putative methionine initiation codon of RbAp48 is surrounded by sequences that resemble the consensus sequence for preferred translational start sites (Kozak, 1984). Also, the DNA sequences upstream from this codon are G+C-rich, and analysis of the codon usage in this region suggests they are non-coding sequences. Further evidence is provided by in vitro translation reactions using transcripts generated from the RbAp48 cDNA, which yield a major protein of 48 kDa (FIG. 2A, lane 2–4, FIG. 2B, lane 2) that co-migrated with the p48 in the eluates of the Rb-affinity columns (FIG. 2B, lane 1).

Another important embodiment of the present invention is the presence of repetitive sequences in the deduced amino acid sequences of p48 and p46. Similar internal repeats have been found in proteins involved in a wide spectrum of cellular functions, including Ste4 in yeast pheromone signal transduction, Cdc4 and Cdc20 in yeast cell cycle control, Tup1in yeast cell identity, sporulation and metabolic repression, etc. (Goebl and Yanagida, 1991). Although the functional significance of the conserved amino acid residues is unknown, site-specific mutagenesis of the tryptophan and aspartic acid residues that occur in these internal repeats, performed in the inventors' laboratory, reveals that these amino acids are important for p48 function in yeast.

Another important aspect of the present invention involves the central role of Ras proteins in growth control in many species and in neoplasia in humans (Barbacid, 1987). The Ras protein sequence is highly conserved throughout eukaryotes and mammalian RAS genes are functional in yeast. Also, mutated yeast RAS genes efficiently transform mouse fibroblast cell lines. Of particular interest is the ability of p48 to suppress the heat shock sensitivity of yeast strains containing a Ras mutation. See, for an example of this function, Example IV, infra. Further studies are required to delineate the exact functional interactions between Rb, p48, p46 and Ras in mammalian cells, however, it is obvious in light of the present disclosure, that the polypeptide and nucleic acid compounds and sequences of the present invention have tremendous utility in increasing the understanding of tumorigenesis and growth and development of healthy human cells.

Isolation of Rb Binding Proteins

Binding of viral proteins to the Rb gene product has inspired a search for cellular binding partners of this important tumor suppressor. Several methods have been shown to be effective in isolating Rb binding proteins. One approach to isolating such proteins is to purify them from cell extracts with Rb protein affinity columns. Example I, infra, provides an example of the preparation and use of an Rb affinity column in the isolation of p48 in the present invention.

Briefly, affinity chromatography is based on the recognition of a protein by a substance such as a ligand or an antibody. The column material is synthesized by covalently coupling a binding molecule, such as a protein, for example to an insoluble matrix. The column material is then allowed to adsorb the desired substance from solution and then the conditions are changed to those under which binding does not occur and the substrate is eluted. The requirements for successful affinity chromatography are that the matrix must not adsorb the target molecules, the ligand must be coupled without altering its binding activity, a ligand must be chosen whose binding is sufficiently tight, and it must be possible to elute the substance without destroying it.

Often, the ligand which is immobilized is a protein which binds a substance, another protein for example, or an antibody that recognizes a particular protein. Various materials are available for immobilizing ligands. Some examples are cyanogen bromide activated agarose, 6-aminohexanoic acid and 1,6 diaminohexane-agarose, epoxy activated agarose, thiopropyl agarose, carbonyldiimidazole activated agarose, and aminoethyl and hydrazide activated polyacrylamide (Freifelder, 1982). While affinity chromatography is a preferred method of isolating p48 from cellular extracts, other ways of purifying the protein exist including those delineated below. It is understood that p48 purified or identified by any of the following methods, or any equivalent methods is encompassed by the present disclosure.

Another approach is to directly test good candidate proteins for their ability to bind the Rb gene product. For example c-myc, N-myc, E2F, ATF-2, and cdc2 proteins are capable of binding Rb protein in vitro. All of these proteins require a carboxyl terminal region of Rb that includes the domain required for binding to the DNA tumor virus transforming proteins. However, these proteins seem to require additional carboxyl terminal sequences that are not required for SV40 T antigen binding.

One preferred method to determine direct binding of two proteins is based on the gel mobility of the proteins. The mobility through a polyacrylamide gel can be determined for each protein individually. The proteins are then mixed and allowed to interact in solution. The mobility of the mixture of the two proteins can be compared to their individual mobilities through separate lanes in a gel matrix under non-denaturing conditions. The appearance of a new, more slowly migrating protein species when the two proteins are mixed indicates binding. The slower migrating species can then be isolated and subjected to SDS-PAGE, during which the two proteins will separate, confirming that the complex is formed of the correct proteins. Proteins can be visualized by standard methods such as silver staining or compass blue dye, for example.

A third possible method for identifying cellular, Rb associated proteins is to screen lambda expression libraries using purified Rb protein as a probe. Several novel genes of unknown function have been identified by this method, and one gene which encodes a protein with properties similar to the transcription factor E2F (Shan et al., 1992; Helin et al., 1992; Kaelin et al., 1992).

Another technique used to isolate Rb associated proteins involves a yeast two-hybrid transcription factor screening system (Chien et al., 1991). Briefly, the Ga14 DNA binding domain is fused to the putative binding domain of Rb. The resulting fusion protein can bind DNA at a GA14 binding sequence, but cannot activate a GA14 dependent promoter since the Ga14 activation domain has been replaced by Rb. A lambda library is constructed that fuses random cDNAs to the transactivation domain of Ga14. If a cDNA encodes a protein that associates with Rb protein, then the Ga14 transactivation domain will be brought into proximity of the DNA binding domain thereby activating transcription from the Ga14 dependent promoter. Activation of the Ga14 dependent promoter serves as the basis for selection and/or screening of the cDNA clones. One advantage of this system, is that binding is detected in a living cell.

Antigen

SV40 T antigen, or a T antigen derived peptide can compete for binding to Rb protein with some cellular proteins, and in particular with p48 binding. The T antigen binds to specific sites in the SV40 DNA sequence and inhibits transcription initiation from the early SV40 promoter. The large T antigen of SV40 complexes preferentially with the underphosphorylated form of the Rb gene product, implying that the underphosphorylated form may be the biologically active form (Ludlow et al., 1989). It is possible that DNA tumor viruses induce transformation by binding the active form of the Rb protein, thereby inhibiting its normal, suppression function (Dyson et al., 1989b). In the process of constructing transgenic mice with SV40 large T antigen under the control of a tissue-specific promoter, a particular line of mice has been identified that expressed large T in the developing retina (Windle et al., 1990). These mice reproducably develop a neoplasm of the eye that is histologically related to human retinoblastoma. The apparent correlation between tumorigenicity of a ira1 strain, the ability of its protein to complex with the Rb gene product, and the induction of retinoblastoma by T antigen suggests that binding of Rb to these viral proteins may have biological relevance. It is also significant that the p48 protein of the present invention competes with T antigen binding to the Rb protein and thus interacts with what is believed to be a biologically important region of Rb.

MSI1

In the yeast *Saccharomyces cerevisiae*, the signal transduction for growth in response to nutrients is mediated by the RAS-cAMP pathway (Tatchell, K., 1986). The yeast RAS proteins play an important role in this process by activating adenylate cyclase, which induces the formation of cAMP (Toda et al., 1985; Broek et al., 1985). The levels of this second messenger regulate, by means of cAMP-dependent protein phosphorylation, the progression of the cell cycle through the early $G_1$ phase (Matsumote et al., 1985).

The ras proteins are highly conserved in evolution (Barbacid, M., 1987). The extended structural homology between the yeast and the mammalian ras proteins suggests that they may serve a fundamental function in cellular proliferation. Mutations in mammalian ras proteins have been associated with cell transformation (Barbacid, M., 1987). Interestingly, the analogous alteration in the yeast RAS2 sequence ($RAS2^{Val19}$) causes defects in the cell cycle control exerted by nutrients (Toda et al., 1985).

IRA1, a gene whose product negatively regulates the RAS-cAMP pathway has been identified (Tanaka et al., 1989). Genetic evidence indicates that this protein may operate on RAS proteins in a manner opposite to the function of the CDC25 protein. IRA1 gene disruption can suppress the lethality of the cdc25 mutation and causes an increased level of intracellular cAMP (Tanaka et al., 1989). These phenotypes are typical of the $RAS2^{Val19}$ mutant, which has a reduced intrinsic GTPase activity (Broek et al., 1985). These observations, together with its partial homology to mammalian GAP (GTPase activating protein) (Vogel et al., 1988), suggest that IRA1 acts to down-regulate RAS activity, and hence adenylate cyclase, by stimulating the GTPase activity of RAS proteins. A suppressor gene of the heat shock sensitive phenotype caused by the viral mutation has also been isolated (Ruggieri et al., 1989). This suppressor gene, MSI1, negatively regulates the cAMP level in response to glucose.

RbAp48 shares sequence homology with MSI1. Furthermore, like MSI1, human RbAp48 suppresses the heat shock sensitivity of the yeast ira1 strains and $RAS2^{Val19}$ strains. Therefore, p48 may provide a link between the heat shock response in yeast and viral transformation/oncogenesis that is known to involve Rb.

In the heat shock experiments, yeast are grown in YPD medium (2% Bacto peptone, 1% Bacto yeast extract, and 2% glucose; or SD medium(0.67% yeast nitrogen base without amino acids, 2% glucose), or SD medium supplemented with auxotrophic requirements. Fresh cells are grown at 25° C. and treated for example, for 20 minutes at 57° C. or 1 hour at 50° C. to induce heat shock. The cells may then be cooled on ice and incubated for about 48 hours at 25° C.

p53 and Heat Shock Proteins

The viral transforming proteins also bind other cellular proteins that may be important in tumorigenesis, including p53 (Linzer and Levine, 1979). Wild type p53 is another tumor suppressor which is frequently found to contain mutations in tumor cells, and that loss of normal p53 expression may be an important step in cell transformation and tumorigenesis (Montenarh, 1992). It is known that the p53 tumor suppressor gene can bind to the heat shock protein/heat shock cognate, 72 hsp/73 hsc, and that a mutant form of p53 is more firmly associated. It has also been demonstrated that Rb binds to the nuclear heat shock cognate 73 hsc (Nihei et al., 1993). Although the biological significance of the association between p53 and heat shock proteins in the oncogenic process is not yet known, it is suggested that these protein associations may play an important role in oncogenesis (Scheffner et al., 1990). This interaction adds another layer of regulation of cell growth and proliferation in which the Rb protein and its effectors are involved. It is essential to understand this pathway of cellular control in order to be able to control tumorigenesis and the discovery of the present invention is an important step in that process of understanding.

Nucleic Acid Hybridization

In addition to their use in directing the expression of the p48 and p46 proteins, the nucleic acid sequences disclosed herein also have a variety of other uses. For example, they also have utility as probes or primers in nucleic acid hybridization embodiments. Oligonucleotide fragments corresponding to the sequence of SEQ ID NO:1 for stretches of between about 10 to 15 nucleotides and about 20 to 30 nucleotides will have utility, as will longer complementary sequences, e.g., those of about 40, 50, 100, 200, 500, 1000, and even up to full length sequences of about 2291 nucleotides in length.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of p46 or p48 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating p48 and p46 genes.

Of course, for some applications, for example, where one desires to prepare mutants employing a mutant primer strand hybridized to an underlying template or where one seeks to isolate p48 or p46-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Detection of Mutations in the p46 and p48 Genes

The DNA sequences of the present invention will find use as probes for detecting mutations in the p46 and p48 genes in the diagnosis and prognosis of certain tumors. Two preferred methods of discovering these mutations are SSCP (single strand conformation polymorphism) and ribonuclease protection assays. The former is based on the understanding that mutations within a DNA molecule will cause that molecule to migrate at a different rate through a denaturing gradient gel such as a polyacrylamide containing a gradient of formamide and urea. The sample DNA is allowed to hybridize to the control (wild type) DNA and then is loaded into the gradient gel. The mutation will cause the duplex to be less stable than a perfectly matched duplex and hence will melt at a lower concentration of urea and formamide. This sample is run in an adjacent lane to a known perfectly matched duplex, such as the double stranded form of the sequences disclosed herein.

Another preferred method is the ribonuclease protection assay. This reaction is typically done with RNase A, which cleaves single stranded RNA preferentially over double stranded RNA. Again, a control, perfectly matched duplex, this time involving at least one strand of RNA is reacted with RNase simultaneously with a sample which may contain one or more mutations, hybridized to the wild type p46 or p48 RNA segment, for example. The RNase will preferentially cleave the RNA at the point of a mismatch, due to the single stranded nature of the duplex at the mismatch. By comparing the fragment size of the control vs. the sample RNA products of this reaction, mutations can be detected. The products can be separated on an agarose gel, for example, and visualized by ethidium bromide staining.

Mutations that affect expression of p46 or p48 in a particular cell may also be detected by immunoprecipitating the proteins from sample cell lysates. In their most simple and direct sense, immunoprecipitation allows the determination of the presence or absence of the particular protein in the lysates of cells. For an example of immunoprecipitation, see Example III, infra.

Another preferred method of detecting p48 or p46 proteins with mutations that affect the conformation of immunoreactivity or the proteins is by Western blotting. Briefly, cells may be harvested, pelleted and dissolved in lysis buffer (50 mM Tris-HCl, 5% β-mercaptoethanol, 2% sodium dodecyl sulfate, 0.1% bromophenol blue, 10% glycerol). Proteins of cell lysates are then separated by polyacrylamide gel electrophoresis in reducing conditions. The gel is then contacted by a nitrocellulose filter, for example and the proteins are transferred to the filter by electroelution, for example. The filters are then incubated in phosphate buffered saline containing 5% bovine serum albumin, washed and incubated with the primary antibody to p46 or p48, washed and then incubated with peroxidase-conjugated goat anti-human IgG secondary antibody (Boehringer Mannheim). The filters are again washed and the color forming reaction is performed using 4-chloro-1-naphtol in methanol with $H_2O_2$, for example.

Biological Functional Equivalents

As mentioned above, modification and changes may be made in the structure of p46 or p48 and still obtain a molecule having like or otherwise desirable characteristics. For example, certain amino acids may be substituted for other amino acids in a protein structure without appreciable loss of interactive binding capacity with structures such as, for example, protein-binding regions of other molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of p46 or p48 proteins or peptides (or underlying DNA) without appreciable loss of their biological utility or activity.

In making such changes, the hydropathic index of amino acids may be considered. The importance of the hydropathic amino acid index in conferring interactive biologic function on a protein is generally understood in the art (Kyte &

Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, antibodies, DNA and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamate and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Epitopic Core Regions

U.S. Pat. No. 4,554,101 (Hopp, incorporated herein by reference) also teaches the identification and preparation of epitopes from primary amino acid sequences on the basis of hydrophilicity. Through the methods disclosed in Hopp one of skill in the art would be able to identify epitopes from within an amino acid sequence such as the p46 or p48 sequence disclosed herein (SEQ ID NO:2). These regions are also referred to as "epitopic core regions".

Numerous scientific publications have been devoted to the prediction of secondary structure, and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1988; Wolf et al., 1988); and also, more recently, new programs for protein tertiary structure prediction (Fetrow & Bryant, 1993).

Antibody Generation and Use

Antibodies, both polyclonal and monoclonal, specific for the p46 or p48 proteins of the present invention may be prepared using conventional immunization techniques, as will be generally known to those of skill in the art. A composition containing antigenic epitopes of p46 or p48 can be used to immunize one or more experimental animals, such as a rabbit or mouse, which will then proceed to produce specific antibodies against p46 or p48. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a p46 or p48-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to p46 or p48.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against p46 or p48. Hybridomas which produce monoclonal antibodies to the selected antigens are identified using standard techniques, such as ELISA and Western blot methods. Hybridoma clones can then be cultured in liquid media and the culture supernatants purified to provide the p46 or p48-specific monoclonal antibodies.

In general, both poly- and monoclonal antibodies against p46 or p48 may be used in a variety of embodiments. For example, they may be employed in antibody cloning protocols to obtain cDNAs or genes encoding p46 or p48 from other species or p46 or p48-like proteins. A particularly useful application of such antibodies is in purifying native or recombinant p46 or p48, for example, using an antibody affinity column. The operation of all such immunological and cloning techniques will be known to those of skill in the art in light of the present disclosure.

Anti-p46 or p48 antibodies may also be used in inhibition studies to analyze the effects of p46 or p48 in cells or animals. Anti-p46 or p48 antibodies will also be useful in immunolocalization studies to analyze the distribution of p46 or p48 during various cellular events, for example, during the cell cycle or during the processes of viral infection of tumorigenesis in cultured cells.

It is proposed that anti-p46 or p48 antibodies will also find useful applications in analyzing the distribution of p46 or p48 throughout the human body, and especially in patients with various cancers such as retinoblastoma. The antibodies may be used to detect p46 or p48, such as in determining p46 or p48 levels. Alternatively, native- or mutant-specific antibodies may be prepared and used to detect native or mutant p46 or p48, to gain qualitative information on p46 or p48 in different patients. Any such anti-p46 or p48 antibodies may be used to detect p46 or p48 species in connection with standard immunochemical procedures, such as immunohistochemical, ELISA and Western blot methods.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

The gene encoding RbAp48 or p48, the retinoblastoma binding protein was cloned from a human HeLa cell cDNA library. The DNA sequence encoding the protein was determined and the deduced amino acid sequence was found to exhibit homology to the MsiI amino acid sequence.

Cloning the RbAp48 Gene

Figure 1A:
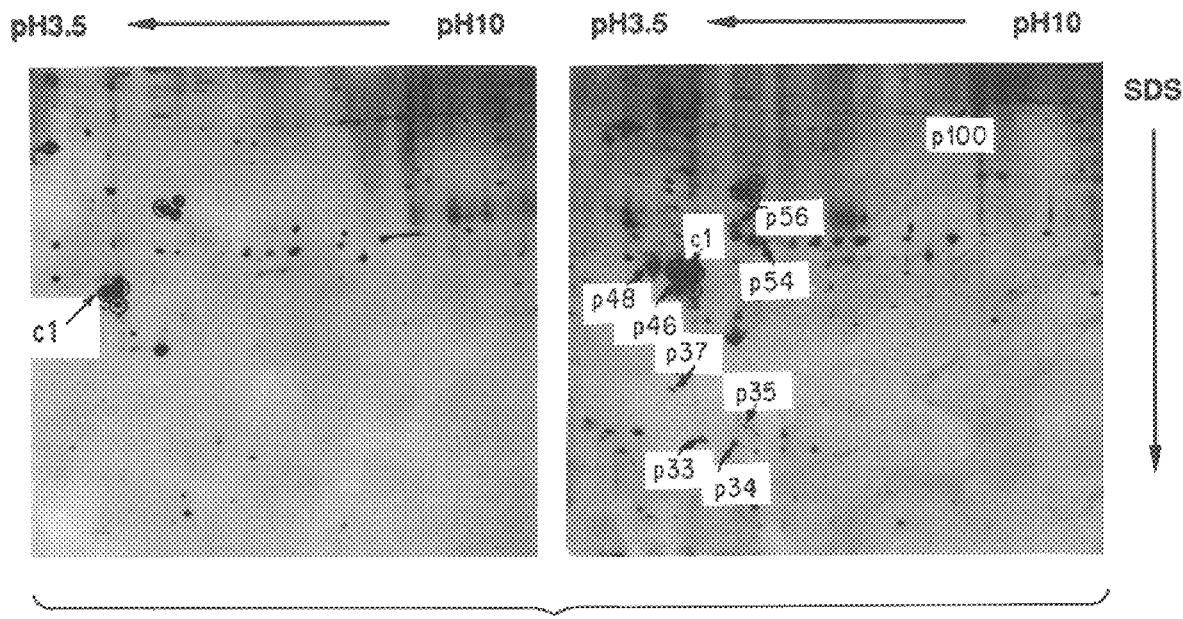
FIG. 1A illustrates the specific interaction between Rb and cellular proteins that bound to the Rb-affinity column. Binding sites in Rb were blocked with either T peptide (left panel) or K peptide (right panel) prior to the addition of the HeLa cell lysate; bound proteins were dissolved in 2-D sample buffer and analyzed on an isoelectric focusing gel.

Several cellular proteins, including E2F, have been shown to interact with the carboxyl terminus of the Rb protein, $p56^{Rb}$ (Lee et al., 1991; Huang et al. 1991; DeFeo-Jones et al., 1991; Kaelin et al., 1991; Kaelin et al., 1992; Helin et al., 1992; Shan et al., 1992). At least nine proteins in HeLa cell lysates or retinoblastoma cell line Weri-24 cell lysates were specifically absorbed to a $p56^{Rb}$ column (Lee et al., 1991; Kaelin et al., 1991). This binding was abolished by pre-incubation of the column with T peptide, a synthetic 18-amino acid polypeptide containing residues 101–118 of T antigen, but not by pre-incubation with K peptide, a mutant version of T peptide (DeCaprio et al., 1989) (FIG. 1A). Competition for binding was also seen with purified T antigen. These results not only indicate the specificity of the interaction between the nine cellular proteins and Rb, but also suggest that the T-binding domains of Rb may be involved in the interaction. The original designation of p46 (Lee et al., 1991) has been changed to p48 and is illustrated in FIG. 1A. p48 in FIG. 1A has a similar but distinct electrophoretic mobility relative to the common protein c1.

A strategy involving microsequencing of purified p48, design of oligonucleotide probes from the partial amino acid sequence, and PCR amplification was employed in the isolation of complementary DNA clones encoding p48. Sequencing of the largest insert revealed a single open reading frame of 425 amino acids with a predicted molecular mass of 47.6 kDa. The two polypeptide sequences obtained from microsequencing of the isolated protein were present within the amino acid sequence deduced from the putative open reading frame. The predicted amino acid sequence of RbAp48 was compared with sequences in GenBank (version 71) and was found to exhibit significant homology with the putative amino acid sequence of the yeast S. cerevisiae MSI1 gene. Msi1 is presumably a negative regulator in the Ras-cAMP pathway in the yeast S. cerevisiae, since overexpression of the MSI1 gene suppresses the heat shock sensitivity of $RAS2^{Val19}$ and ira1 mutants, and reduces the cAMP level in these mutants (Ruggieri et al., 1989). The predicted p48 and Msi1 amino acid sequences share 30% identity (46% similarity) over their entire lengths. Interestingly, internal repeats, which were first identified in the transducin b subunit (Fong et al., 1986), are present in both p48 and Msi1 proteins.

Methods $p56^{Rb}$ was expressed in E. coli as previously described (Huang et al., 1991) except that IPTG induction was performed at 30° C. for 3 h. $p56^{Rb}$ affinity matrixes were produced by the cross-linking of approximately 1 mg of purified $p56^{Rb}$ to 1 ml (bed volume) of Affi-Gel 10 resin (Bio-Rad) according to the manufacturer's instructions. HeLa cells, 1×10⁹, were lysed in 10 ml EBC buffer (50 mM Tris-HCl, pH 8.0, 120 mM NaCl, 0.5% Nonidet P-40, 1 mM β-mercaptoethanol, 1 mM EDTA, 200 U ml⁻¹aprotinin, 200 U ml⁻¹ leupeptin, 1 mM PMSF, 1 mM NaF). The lysate was clarified by centrifugation at 35,000 r.p.m. for 30 min at 4° C. followed by filtration using 0.45 mm filter.

For binding competition, 100 ml of Rb matrices were first incubated with 0.5 ml EBC buffer containing 0.3 mM T peptide or K peptide for 1 h at 4° C. followed by the addition of 1 ml lysate and further incubation at 4° C. for 1 h. The amino-acid sequence of T peptide is ENLFCSEEMPSSD-DEAAT (SEQ ID NO:3), and K peptide is ENLFC-SKEMPSSDDEAAT (SEQ ID NO:4). After extensive washing with NET buffer(50 mM Tris-HCl, pH 8.0, 0.2 M NaCl, 1 mM EDTA, 1 mM β-mercaptoethanol, 1 mM PMSF, 1 mM NaF), bound proteins were released from matrixes using 2-D sample buffer (1.2g urea, 100 ml ampholines, pH3.5–10, 400 ml 10% NP-40, 20 ml β-mercaptoethanol, 680 ml H₂O) and resolved by isoelectric focusing in a pH 3.5–10.0 gradient containing 155 ml of pH 3.5–10.0 ampholine (LKB) with 310 ml of pH 5.0–7.0 ampholine (LKB) per 10 ml of gel solution followed by fractionation using SDS polyacrylamide gel electrophoresis (Lee et al., 1991).

Proteins were visualized by silver staining (FIG. 1A). For amino acid sequencing, compass-blue stained gel pieces containing about 20 mg of p48 were collected from 2-D gels and digested with CNBr in situ. The resultant peptides were separated in a 15% SDS-polyacrylamide gel and transferred onto a polyvinylidene difluoride (PVDF) membrane (Millipore) according to Matsudaira (1989). The membrane was stained with 0.1% Coomassie blue in 50% (v/v) methanol for 5 min and washed with water. Pieces of membrane containing CNBr fragments were used directly for microsequencing. Two peptide sequences (underlined in FIG. 1B) were obtained.

Two degenerate oligonucleotides were synthesized for the polymerase chain reaction (PCR) using first strand cDNA synthesized from fetal brain RNA templates. The forward PCR primer was GAR GAY ACH GTB GAR GAR MG (SEQ ID NO:7); the reverse PCR primer was GTR TTY TTY TTC CAR ATY TTR TA (SEQ ID NO:8). The PCR reaction was carried out in a reaction mixture containing 4 μg forward primer, 4 μg reverse primer, and 1 U Taq polymerase (Perkin-Elmer-Cetus). Amplification conditions were 30 cycles of 93° C. for 1 min, 50° C. for 1 min and 72° C. for 1 min. This reaction generated one band of 60 basepairs (bp) which was subcloned, sequenced and shown to encode the previously determined peptide sequences. A HeLa cell Lambda gt11 cDNA library was then screened with the 60 bp fragment. Of ~8.2×10⁵ bacteriophage screened, thirteen bacteriophage contained inserts that hybridized with the oligonucleotide probe in a Southern blot analysis.

EXAMPLE II

In order to determine whether the gene isolated from the cDNA library encodes the protein isolated from the affinity column, comparisons were made based on the size and immunogenicity of the isolated and the recombinant proteins.

RbAp48 Encodes p48

Figure 2C:
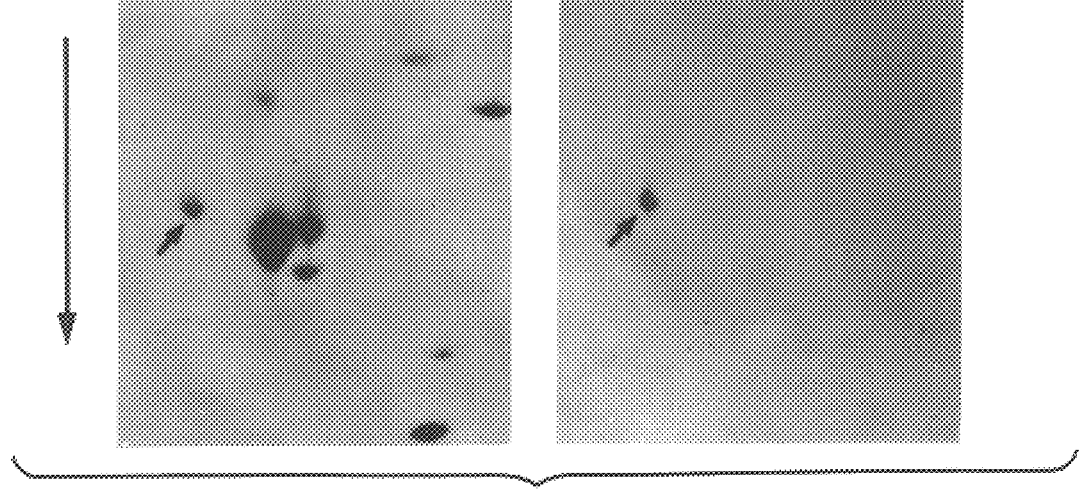
FIG. 2C shows the immunoreactivity of antibody 13D10 with p48 on a 2-D gel. Rb matrices were incubated with a mixture of radiolabeled and unlabeled HeLa cell lysates. Bound proteins were separated by 2-D gel electrophoresis and visualized by immunoblotting with 13D10 (right panel), followed by fluorography (left panel). The arrow indicates the p48 spot detected by antibody 13D10.

To further confirm that the cDNA clone encodes p48, the protein was overexpressed in *E. coli* and antibodies were raised against the putative p48 purified from the bacteria. These polyclonal antibodies recognize authentic p48 and p46 in the Rb-affinity column eluates. In addition, monoclonal antibodies that recognize p48 were produced. Several monoclonal antibodies including 13D10 recognized only one protein in the Rb-affinity column eluates (FIG. 2C, right panel). The immunoreactive protein co-localizes with p48 in the autoradiograph of the 2-D gel in FIG. 2C, left panel. Based on the sequence analysis and the immunological data, it is the inventors' conclusion that RbAp48 encodes p48.

Methods

The unmodified RbAp48 transcript was synthesized using T7 RNA polymerase, and a Kpn I linearized pGEM-RbAp48 plasmid template containing a 2.2 kb RbAp48 cDNA fragment inserted into the EcoR I site of the vector pGEM-3Z. The chimeric RbAp48 transcript was synthesized using SP6 RNA polymerase, and an EcoRI linearized pb-RbAp48 plasmid that contains the RbAp48 coding region inserted into the NcoI-EcoRI sites of the plasmid pB10 (Huang et al., 1990). The resulting capped transcripts were translated in reticulocyte lysates according to the manufacturer's instructions (Promega). Protein products were separated by SDS-PAGE directly or were immunoprecipitated with anti-p48 monoclonal antibody 13D10 prior to loading.

A 5 ml aliquot of the translation product using pb-RbAp48 as the template was resuspended in 0.3 ml EBC buffer, and mixed with 15 ml of 13D10 (100 mg ml⁻¹) on ice for 1 h. Fifty microliters of protein G-Sepharose beads in EBC containing 4% BSA was added and the mixture was rocked at 4° C. for 1 h. The beads were subsequently washed once with EBC buffer, three times with EBC buffer containing 1 M NaCl, and once again with EBC buffer. Five microliters of translation products in the absence of RNA or in the presence of RNA from pGEM-RbAp48, and 1 ml translation product with RNA from pb-RbAp48 were analyzed on a 10% SDS-polyacrylamide gel. The resulting fluorographs are shown in FIG. 2A.

A comparison of the affinity chromatography eluted protein and the in vitro translation product is shown in FIG. 2B. Eluates were prepared as described in FIG. 1 except bound proteins were released from matrices by boiling in SDS sample buffer for 5 min. Eluates, and 1 ml of the translation product of RNA from pb-RbAp48 were separated on a 10% SDS-polyacrylamide gel and transferred onto a PVDF membrane by standard techniques. The membrane was first incubated with blocking buffer, then monoclonal antibody 13D10, followed by alkaline phosphatase-conjugated goat anti-mouse IgG.

Rb matrices were incubated with lysates from 5×10⁶ cells labeled with ³⁵S-methionine and 1×10⁸ unlabelled HeLa cells. Bound proteins were separated in a 2-D gel and incubated with antibody 13D10 (FIG. 2C, right panel). The filter was then visualized by fluorography (FIG. 2C, left panel).

EXAMPLE III

The interaction between p48 and Rb protein was studied by several different approaches. First, purified p48 and p56 were incubated together prior to the addition of anti-Rb polyclonal antibodies. p48 was co-immunoprecipitated by anti-Rb antibody 0.495 (Wang et al., 1990). Second, binding of p48 and Rb was examined in vivo using tumor cell lines with and without Rb mutations.

In vivo and in Vitro Interaction of Rb and p48

Figure 3A:
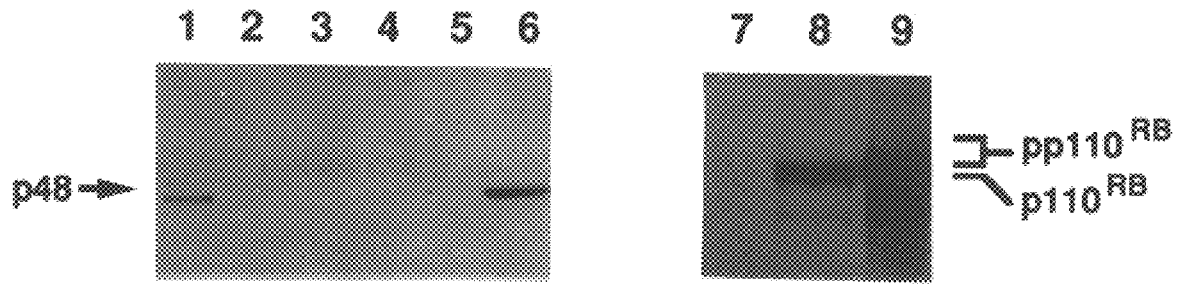
FIG. 3A is a gel in which lysates were prepared from 6 cell lines; HeLa (lane 1), Weri-27 (lane 2), DU-145 (lane 3), SaoS-2 (lane 4), SCLC-SD-1 (lane 5), Molt-4 (lanes 6–9). Equal amounts of total protein (38 mg) were aliquoted for immunoprecipitation using anti-Rb 0.495 (lanes 1–6 & 9), anti-p48 13D10 (lane 8) or normal serum (lane 7). The immunoprecipitates were separated by denaturing gel electrophoresis, transferred to a membrane and incubated with anti-p48 antibody 13D10 (lane 1–6) or anti-Rb 3C8 (lane 7–9).
Figure 3C:
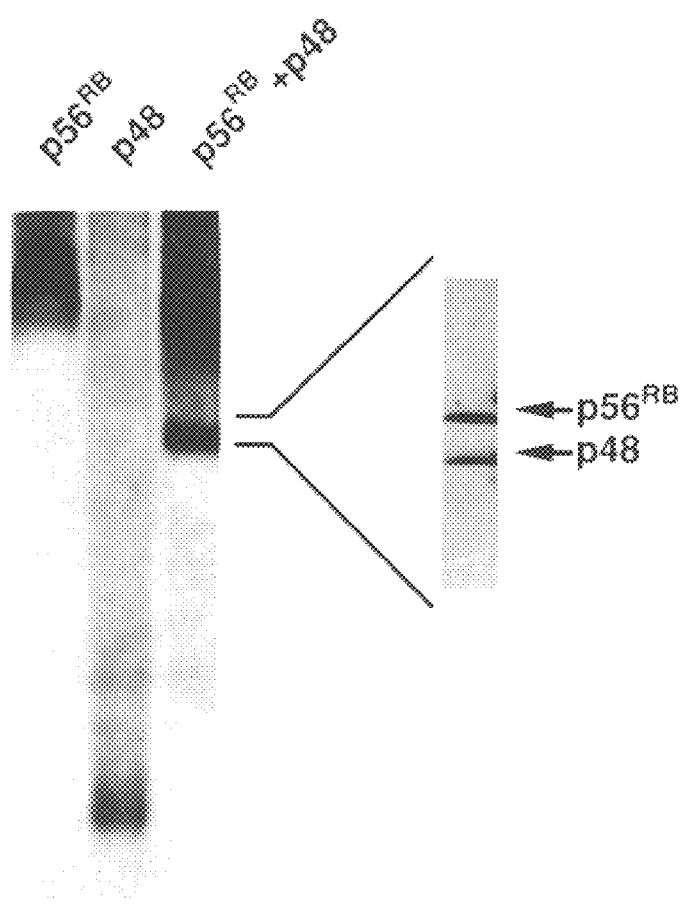
FIG. 3C demonstrates direct binding between p56$^{Rb}$ and p48. In the left panel, purified p56', p48, and a mixture of p56' and p48 were separated by native polyacrylamide gel electrophoresis and visualized by silver staining. In the right panel, a new band seen in the p56w and p48 mixture was excised and the proteins were separated on a 10% SDS-polyacrylamide gel and visualized by silver staining.
Figure 3B:
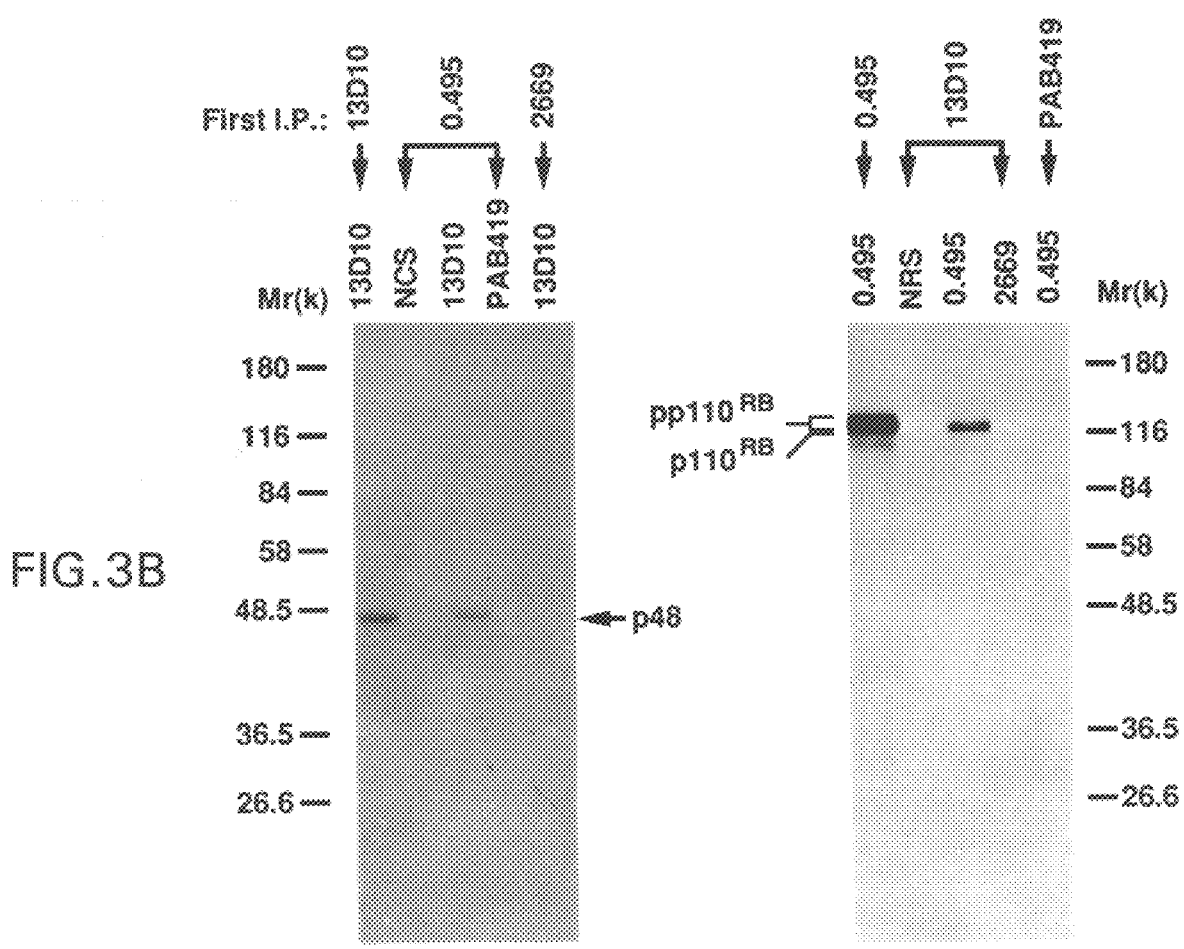
FIG. 3B shows the result of an immunoprecipitation. Molt-cells were labeled with $^{35}$S-methionine and lysed as described above. The lysate was first immunoprecipitated with either anti-Rb antibody 0.495 or anti-p48 antibody 13D10. The resulting immune complexes were boiled in the presence of 2% SDS to dissociate protein complexes, and the denatured proteins were diluted for reimmunoprecipitation with the indicated antibodies. Normal culture supernatant for hybridoma (NCS), normal rabbit serum (NRS), rabbit anti-nm23 antibody 2669 (unpublished), and PAB419 (Harlow et al., 1981) were used as negative controls. In the samples where 13D10 or 0.495 immunoprecipitates were reimmunoprecipitated with the same antibodies, only one-tenth of the samples were loaded onto the gel.

In co-immunoprecipitation experiments with anti-Rb antibody, p48 was co-precipitated with Rb in cells expressing wild-type Rb (HeLa and Molt-4; FIG. 3A, lanes 1 & 6) but not in cells that lack Rb due to a complete deletion of the gene (FIG. 3A, lane 2), nor in cells known to have deletions within the T-binding domains of Rb (FIG. 3A, lanes 3–5). p48 is present in all the cell types used in this study. In similar experiments with anti-p48 antibody, only unphosphorylated and hypophosphorylated forms of the Rb protein were co-precipitated with p48 (FIG. 3A, lanes 8 & 9). The in vivo association of Rb with p48 was also demonstrated by sequential immunoprecipitations with ³⁵S-methionine labeled cells. As shown in FIG. 3B, anti-p48 antibody 13D10 specifically recognized p48 present in immune complexes formed with anti-Rb antibody 0.495 (FIG. 3B, left panel). Conversely, anti-Rb antibody 0.495 specifically re-immunoprecipitated only the unphosphorylated and hypophosphorylated forms of Rb protein from immune complexes formed with anti-p48 antibody 13D10 (FIG. 3B, right panel).

It was also contemplated that p48 may interact directly with Rb. Under appropriate conditions, p48 and p561 each migrated as a single broad band on a non-denaturing polyacrylamide gel (FIG. 3C). When the two proteins were incubated together prior to electrophoresis, a new protein band was identified (FIG. 3C, left panel). This new band contains p48-Rb complexes, as shown by excision of the band followed by separation of the individual proteins by SDS polyacrylamide gel electrophoresis (FIG. 3C, right panel). Similarly, complexes are formed between p48 and full-length Rb. Since Rb is a nuclear protein (Lee et al., 1987), it is expected that interaction between p48 and Rb takes place in the nucleus. Subcellular fractionation and immunocytochemistry studies done by the inventors demonstrate that p48 is also a nuclear protein.

Methods

Whole cell lysates were prepared as described in FIG. 1. The lysates were incubated with the appropriate antibodies on ice for 1 h. Fifty microliters of protein G-Sepharose beads in EBC containing 4% BSA were added and the mixtures were rocked at 4° C. for 2 h. The beads were subsequently washed three times with NET buffer, and twice with EBC buffer. The resulting immune complexes were released from the beads by boiling in SDS sample buffer for 10 min and then analyzed by immunoblotting (FIG. 3A).

The first immunoprecipitation was carried out as described above. The resulting immune complexes were boiled in the presence of 2% SDS to dissociate protein complexes according to Helin et al. (1992). The denatured proteins were diluted 25-fold with EBC buffer containing 3 mg ml⁻¹ BSA and re-immunoprecipitated with additional antibody as indicated. The beads were subsequently washed three times with EBC buffer containing 1 M NaCl, and twice with EBC buffer. The resulting immune complexes were dissociated from the beads by boiling in SDS sample buffer and separated in a 10% SDS-polyacrylamide gel. The proteins were visualized by fluorography (FIG. 3B).

The NcoI-BamHI fragment of p48 cDNA was inserted into the NcoI and BamHI sites of pET8c vector (Studier et al., 1990). The resulting plasmid pET-48NB encodes a chimeric p48 protein containing a modified C-terminus (five C-terminal amino-acids of p48, EGQGS (SEQ ID NO:5), were replaced by eighteen amino-acids, AANKARKEAELAAANAEQ, SEQ ID NO:6). This plasmid was transformed into the host cell, BL21(DE3)pLysS and transformants were grown to an $OD_{600}$ of 0.6–1.0 at 37° C. in LB media containing 100 mg ml$^{-1}$ ampicillin and 25 mg ml$^{-1}$ chloramphenicol. The growth temperature was reduced to 30° C., and IPTG was added to a final concentration of 0.4 mM. The bacteria were collected 3 h later and lysed in EBC buffer by freezing, thawing, and sonicating. The inclusion body was collected by centrifugation at 10,000 r.p.m. for 10 min. The pellet was extensively washed with EBC buffer. The washed inclusion body was dissolved in 8 M urea and then successively dialyzed against 6 M urea, 4 M urea, 2 M urea, 1 M urea, and finally in renaturation buffer (0.2 M Tris-HCl, pH 8.0, 0.5 M NaCl) for 12 h. The refolded protein was further purified by gel filtration using a Sephacryl S-300 column equilibrated with S-300 buffer (20 mM sodium phosphate, pH 7.5, 200 mM NaCl, 1 mM EDTA, 1 mM β-mercaptoethanol, 10% glycerol). Half microgram of $p56^{Rb}$, 0.2 mg of p48, and a mixture of both in 5X Tris-Glycine buffer (0.125 M Tris-Glycine, pH 8.8) were separated on a 6% native-polyacrylamide gel. Electrophoresis was carried out in 1X Tris-Glycine buffer (See FIG. 3C).

EXAMPLE IV

Because of the similarity between the putative amino acid sequences of p48 and Msi1, the ability of a cDNA encoding p48 to suppress the heat shock sensitivity of the two yeast mutant strains, $RAS2^{Val19}$ (TK161-R2V), and ira1 (KT6-1A–D) was tested.

Heat Shock Suppression by p48

Figure 4:
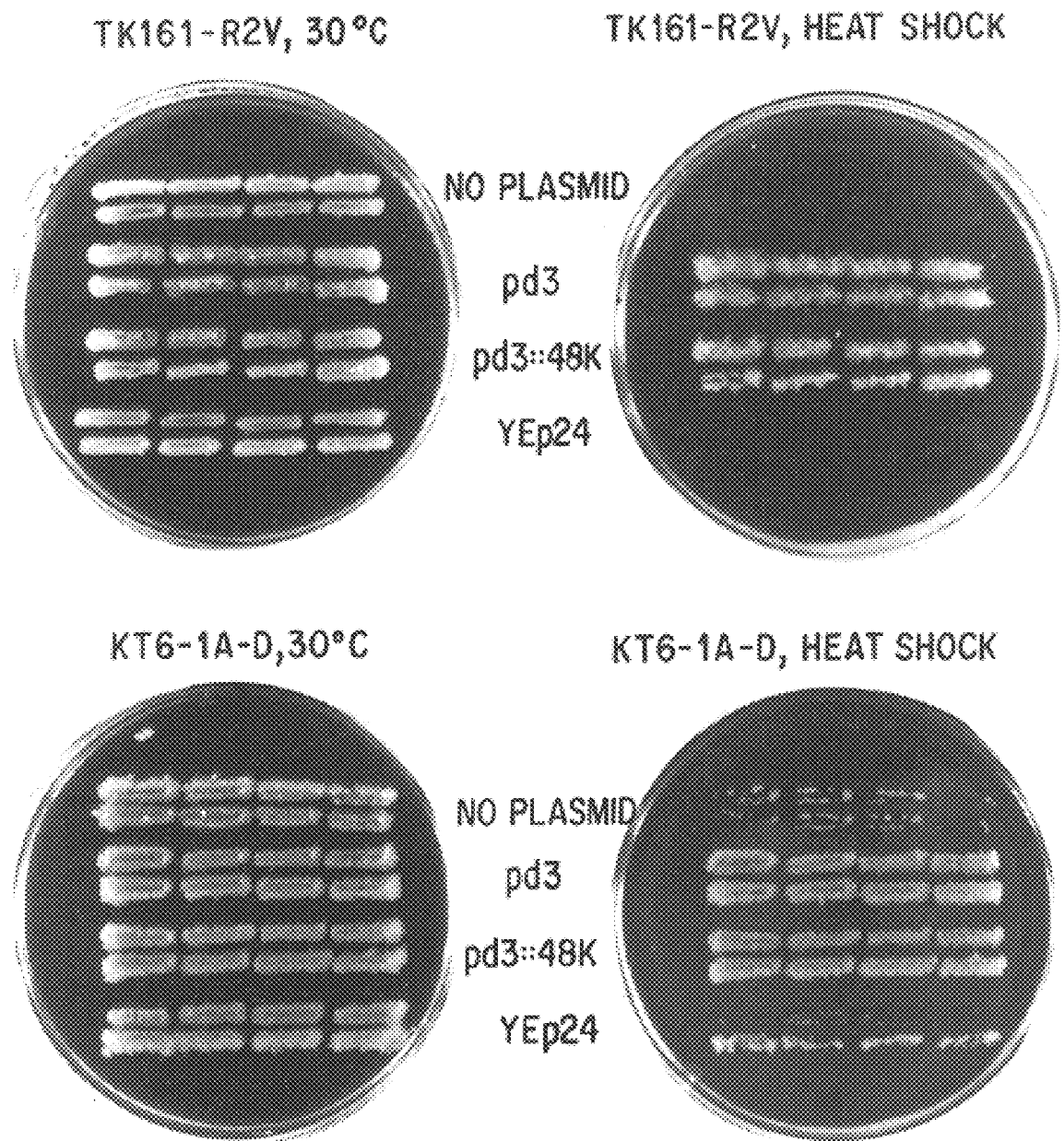
FIG. 4 shows the effect of p48 expression on the heat shock sensitivity of yeast strains containing RAS2$^{Val19}$ and yeast strains lacking ira1. The top left and right plates indicate the heat shock resistance of yeast strains TK161-R2V, carrying RAS2$^{Val19}$ after transformation with the various indicated plasmids: A control with no plasmid; pd3, a plasmid expressing yeast MSI1 under its own promoter; pd3::48K, a plasmid expressing human p48 from the yeast MSI1 promoter; and YEp24, the vector from which pd3 is derived are shown. One of the replicate plates containing the transformant patches was incubated at 30° C. (left), and the other was incubated at 57° C. prior to incubation at 30° C. (right). The bottom left and right plates show the heat shock resistance of yeast strains KT6-1A–D, which contain a disrupted chromosomal ira1 gene after transformation and incubation as in the upper plates.

Introduction of either pd3, the yeast MSI-containing plasmid, or pd3: :p48, but not control plasmid YEp24 conferred complete resistance to heat shock (FIG. 4). YEp24-transformed and untransformed KT6-1A–D cells did grow slightly after heat shock presumably due to the low level heat shock resistance of the ira1 mutant strain (Ruggeri, personal communication). However, the survival level was well below that of the cells that were transformed with the MSI and p48 containing plasmids.

To confirm that heat shock resistance was due to the pd3: :p48 plasmid itself, plasmid loss analyses were performed. These analyses demonstrated that all transformants that lose the pd3: :p48 plasmid no longer survive heat shock. In addition, similar results were obtained using the pYC::p48 in which the RbAp48 gene is transcribed under the control of the strong yeast ADH1 promoter. Although the mechanism of heat shock resistance is unknown, these data provide evidence that RbAp48 is functional in yeast, and p48 mimics the function of Msi1 in yeast.

Methods

Strains TK161-R2V (MATa $RAS2^{Val19}$ leu2 ura3 trp1 his3 ade8 can1) and KT6-1A–D (MATa/MATa ira1::LEU2/ira1::LEU2 ura3/ura3 leu2/leu2 trp1/trp1 his3/his3) and plasmid pd3 (MSI1 URA3) (Ruggieri et al., 1989) were kindly provided by R. Ruggieri. Plasmid pd3::48K was constructed by replacing the ClaI-Xho I coding region of the MSI1 gene on pd3 with the Nco I-Kpn I coding region of the RbAp48. This yielded an in-frame fusion between MSI1 codon 17 and RbAp48 codon 1, effectively substituting the entire open reading frame for that of MSI1. This plasmid, as well as pd3 and control vector YEp24 were transformed into each of the yeast strains by the spheroplast method (Sherman et al., 1986). Transformants were patched onto selective medium plates, and after one day of growth at 30° C., were replica-plated onto two rich medium plates. One of these plates was incubated for two days at 30° C., while the other was heat-shocked by incubation at 57° C. for 20 min (TKK161-R2V) or 30 min (KT6-1A–D) prior to incubation for 2 days at 30° C. The longer heat shock period was used for KT6-1A–D since this strain is known to be partially resistant to heat shock, possibly due to occasional reversion of the ira1::LEU2 insertion.

EXAMPLE V

A gene encoding p46, the retinoblastoma binding protein has also been cloned from a human HeLa cell library. The nucleic acid sequence of the gene has been determined and the deduced amino acid sequence compared to the p48 amino acid sequence. The amino acid sequences share a 95% homology, but significant differences exist in the 5' and 3' untranslated regions, indicating that these two proteins are encoded by different genes.

Cloning the RbAp46 gene

Polyclonal and monoclonal antibodies to the p48 protein were found to crossreact with the p46 protein in a Western Blot analysis. One of these monoclonal antibodies was chosen to screen a lambda gt11 expression library created from human HeLa cells for a clone expressing the p46 protein. A full-length cDNA was isolated by this method. Sequence analysis revealed a 425 amino acid open reading frame which shares a 95% amino acid homology with p48 as seen in FIG. 6.

EXAMPLE VI

It is contemplated that p46 or p48 will have utility in suppressing the oncogenic p21 RAS in human tumor cells. RAS point mutations have been found in diverse tumor types ranging from leukemias to colorectal carcinomas. The Ras signal pathway is believed to be highly conserved in eukaryotic organisms. The inventors have demonstrated that p46 or p48 can suppress the heat shock phenotype in a yeast strain carrying a RAS mutation (See Example IV, infra). It is therefore plausible that overexpression of p46 or p48 can suppress the activity of oncogenic RAS in mammalian cells.

Use of p46 or p48 in Treatment of Human Tumors

Preliminary findings indicate that the level of expression of p48 or p46 is important in their biological function. Therefore, it is contemplated that the intracellular levels of these proteins can be regulated by techniques available in the art. For example, p46 or p48 levels can be increased by infecting cells with a retroviral or an adenoviral vector which expresses the desired protein at higher levels necessary for suppression of mutations in the Rb gene or in other oncogenic or tumor suppressor genes. Alternatively, levels of these proteins can be reduced in the cells by inserting antisense oligonucleotides to suppress expression of the protein products in the cell. Oligonucleotides may be inserted into specific cells by methods known in the art, such as by polycationic carriers or by encapsulation in lipid vectors.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bandara and LaThangue (1991) *Nature* 351:494–497.
Barbacid, M. (1987) *Ann. Rev. Biochem.* 56, 779–827.
Berer, D. and Young, T. (1982) *Nature* 300:724.
Broek et al. (1985) *Cell* 41:763–769.
Chien, C.-T., Bartel, P. L., Sternglanz, R. and Fields, S. (1991) *Proc. Natl. Acad. Sci. USA*. 88: 9578–9582.
Chou and Fasman, *Biophys. J.*, 26:367–384, 1979.
Chou and Fasman, *Biochemistry*, 13(2):222–245, 1974a.
Chou and Fasman, *Ann. Rev. Biochem.*, 47:251–276, 1978b.
Chou and Fasman, *Adv. Enzymol. Relat. Areas Mol. Biol.*, 47:45–148, 1978a.
Chou and Fasman, *Biochemistry*, 13(2):211–222, 1974b.
DeCaprio, J. A., Ludlow, J. W., Figge, J., Shew, J.-Y., Huang, C.-M., Lee, W.-H., Marsillo, E., Paucha, E. and Livingston, D. M. (1988) *Cell* 54:275–283.
DeCaprio, J. A., et al. (1989) *Cell* 58, 1085–1095.
DeFeo-Jones, D., et al. (1991) *Nature* 352, 251–254.
Draetta, G. (1990) *Trends Biochem. Sci.* 15:378.
Dunn, J. M., Phillips, R. A., Becker, A. J. and Gallie, B. L. (1988) *Science* 241:1797–1800.
Dyson, N., Buchkovich, K., Whyte, P. and Harlow, E. (1989a) *Cell* 58:248–255.
Dyson, N., Howley, P. M., Munger, K. and Harlow, E. (1989b) Science. 243:934–937.
Ewen, M. E., Ludlow, J. W., Marsilio, E., DeCaprio, J. A., Millikan, R. C., Cheng, S. H., Paucha, E. and Livingston, D. M. (1989) *Cell* 58:257–267.
Fong, H. K. W., et al. (1986) *Proc. Natl. Acad. Sci. USA* 83, 2162–2166.
Freifelder, David ed.,*Physical Biochemistry*, 2nd edition, Freeman and Company, San Francisco, Calif., 1982.
Goddard, A. D., Balakier, H., Canton, M., Dunn, J., Squire, J., Reyes, E., Becker, A., Phillips, R. A. and Gallie, B. (1988) *Mol. Cell. Biol.* 8:2082–2088.
Goebl, M. & Yanagida, M. (1991) *TIBS* 16, 173–177.
Goodrich, D. W. & Lee, W.-H. (1993) *Biochim. Biophy. Acta in press.*
Harlow, E., Crawford, L. V., Pim, D. C. & Williamson, N. M. (1981) *J. Virol.* 39, 861–869.
Harris, H. (1986a) *J. Cell. Sci. Suppl.* 4:431–444.
Helin, K., et al. (1992) *Cell* 70, 337–350.
Hopp, U.S. Pat. No. 4,554,101
Horowitz, J. M., Park, S.-H., Bogenmann, E., Cheng, J.-C., Yandell, D. W., Kaye, F. J., Minna, J. D., Dryja, T. P. and Weinberg, JR. A. (1990) *Proc. Natl. Acad. Sci. USA* 87:2775–2779.
Hu, Q. J., Lees, J. A., Buchkovich, K. J. and Harlow, E. (1992). *Mol. Cell. Biol.* 12, 971–980.
Huang, S., Lee, W.-H. & Lee, E. Y.-H.P. (1991) *Nature* 350, 160–162.
Huang, S., Wang, N.-P., Tseng, B. Y., Lee, W.-H. & Lee, E. Y.-H.P. (1990) *EMBO J* 9, 1815–1822.
Ikawa and Weinberg (1992) *Proc. Natl. Acad. Sci. USA* 89:2012–2016.
Jameson and Wolf, *Comput. Appl. Biosci.*, 4(1):181–186, 1988.

Jobling, S. A. & Gehrke, L. (1987) *Nature* 325, 622–625.
Kaelin, W. G. J., Pallas, D. C., DeCaprio, J. A., Kaye, F. J. & Livingston, D. M. (1991) *Cell* 64: 521–532.
Kaelin, W. G., et al. (1992) *Cell* 70: 351–364.
Klein, G., Bregula, U., Wiener, F. and Harris, H. (1971) *J. Cell Sci.* 8:659–672.
Kozak, M. (1984) *Nucleic Acids Research* 12:858–872.
Kyte & Doolittle (1982) *J. Mol. Biol.* 157:105–132.
Lee, W.-H, Bookstein, R., Hong, F., Young, L.-J., Shew, J.-Y., and Lee., E. Y.-H. P. (1987a) *Science* 235:1394–1399.
Lee, W.-H., Shew, J.-Y., Hong, F., Sery, T., Donoso, L. A., Young, L. J., Bookstein, R. and Lee, E. Y.-H. P. (1987b) *Nature* 329:642–645.
Lee, W.-H., et al. (1991) *Cold Spring Harbor Sym. Quant. Biol.* 56:211–217.
Levine, A. J., Momand, J. and Finlay, C. A. (1991) *Nature* 351:453–456.
Ludlow J. W., decaprio, J. A., Huang, C.-M., Lee, W.-H., Paucha, E., and Livingston, D. M. (1989) *Cell* 56:57–65.
Manfredi, J. J. and Prives, C. (1990) *J. Virol.* 64:5250–5259.
Matsudaira, P. T. *A practical guide to protein and peptide purification for microsequencing.* (Academic Press, Inc., San Diego, 1989).
Matsumote et al., 1985, *Yeast* 1:15–24.
Migdal, C. (1976) *Br. J. Opthalmol.* 60:151.
Montenarh, M. (1992) *Critical Reviews in Oncogenesis* 3:233–256.
Nihei et al. (1993) *Cancer Research* 53:1702–1705.
Ruggieri, R., et al. (1989) *Proc. Natl. Acad. Sci. USA* 86, 8778–8782.
Sambrook et al. (1989) Molecular Cloning: A Laboratory Manual, Cold Spring Harbor Laboratory, Cold Spring Harbor, N.Y.
Scheffner et al. (1990) *Cell* 63:1129–1136.
Shan, B., et al. (1992) *Mol. Cell. Biol.* 12:5620–5631.
Sherman, F., Fink, G. & Hicks, J. *Laboratory course manual for methods in yeast genetics (Cold Spring Harbor, N.Y., 1986).*
Shields, J. A. (1983) In *Diagnosis and Management of Intraocular Tumors.* (C. V. Mosby, St. Louis). Pages 437–438.
Studier, F. W., Rosenberg, A. H., Dunn, J. J. & Dubendorff, J. W. (1990) *Methods in Enzymology* 185:60–89.
Tanaka et al. (1989) *Mol. Cell. Biol.* 9:757–768.
Tatchell, K. (1986) *J. Bacteriol.* 166:364–367.
Templeton, D. J., Park, S. H., Lanier, L. and Weinberg, R. (1991) *Proc. Natl. Acad. Sci. USA* 88:3033–3037.
Templeton, D. J. (1992) *Mol. Cell. Biol.* 12:435–443.
Toda et al. (1985) *Cell* 40:27–36.
Vogel et al. (1988) *Nature (London)* 335:90–93.
Vogel, F. (1979) *Hum. Genet.* 1–54.
Wang, N.-P., et al. (1990) *Cell Growth Differ.* 1:233–239.
Weber, J. M., Sircar, S., Rodrigues, M., Cai, F. and Horvath, J. (1991) *Oncogene.* 6:989–993.
Weischelbaum, R. R., Beckett, M. and Diamond, A. (1988) *Proc. Natl. Acad. Sci. USA* 85:2106–2109.
Whyte et al. (1988) *Nature* 334:124–129.
Wolf et al., (1988) Comput. Appl. Biosci., 4(1):187–191.

What is claimed is:

1. An isolated DNA molecule comprising DNA encoding a p48 protein or polypeptide having the amino acid sequence of SEQ ID NO:2.

2. The DNA molecule of claim 1, wherein said DNA has the nucleic acid sequence of SEQ ID NO:1.

3. An isolated DNA molecule comprising DNA encoding a p46 protein or polypeptide having the ammo acid sequence of SEQ ID NO:10.

4. The DNA molecule of claim 3, wherein said DNA molecule has the nucleic acid sequence of SEQ ID NO:9.

5. The DNA molecule of claim 1 or claim 3, wherein said DNA is positioned under the control of a promoter.

6. The DNA molecule of claim 5, wherein said DNA is positioned under the control of a recombinant promoter.

7. The DNA molecule of claim 1 or claim 3 further defined as a recombinant vector.

8. The DNA molecule of claim 7, wherein said vector is a recombinant expression vector capable of expressing a p48 protein or polypeptide on introduction into a host cell.

9. The DNA molecule of claim 8, wherein said vector comprises a nucleic acid sequence in accordance with SEQ ID NO:1.

10. The recombinant vector of claim 7, wherein said vector is a recombinant expression vector capable of expressing a p46 protein or polypeptide on introduction into a host cell.

11. The recombinant expression vector of claim 10 wherein said vector comprises a nucleic acid sequence in accordance with SEQ ID NO:9.

12. The recombinant expression vector of claim 7, wherein said vector is a multicopy plasmid.

13. The recombinant expression vector of claim 7, wherein said vector is capable of being transformed into and expressed in a yeast host cell.

14. The recombinant expression vector of claim 7, wherein said vector is derived from plasmid YEp13.

15. A recombinant host cell comprising a DNA molecule in accordance with claim 1 or claim 3.

16. The recombinant host cell of claim 15, wherein said host cell is a prokaryotic cell.

17. The recombinant host cell of claim 15, wherein said host cell is a eukaryotic cell.

18. The recombinant host cell of claim 17 wherein said cell is a yeast cell.

19. The recombinant host cell of claim 15, wherein said DNA molecule is introduced into the cell by means of a recombinant vector.

20. The recombinant host cell of claim 19, wherein said recombinant vector is an expression vector and said host cell expresses a recombinant p48 protein or polypeptide.

21. The recombinant host cell of claim 20, wherein said expression vector comprises a nucleic acid sequence in accordance with the nucleic acid sequence of SEQ ID NO:1.

22. The recombinant host cell of claim 19, wherein said recombinant vector is an expression vector and said host cell expresses a recombinant p46 protein or polypeptide.

23. The recombinant host cell of claim 22, wherein said expression vector comprises a nucleic acid sequence in accordance with the nucleic acid sequence of SEQ ID NO:9.

24. An isolated nucleic acid molecule which comprises at least a 30 nucleotide long stretch which corresponds to the nucleic acid sequence of SEQ ID NO:1.

25. The nucleic acid molecule of claim 24, further defined as comprising at least a 50 nucleotide long stretch which corresponds to the nucleic acid sequence of SEQ ID NO:1.

26. The nucleic acid molecule of claim 25, further defined as comprising at least a 100 nucleotide long stretch which corresponds to the nucleic acid sequence of SEQ ID NO:1.

27. The nucleic acid molecule of claim 26, further defined as comprising at least a 1000 nucleotide long stretch which coresponds to the nucleic acid sequence of SEQ ID NO:1.

28. The nucleic acid molecule of claim 27, further defined as comprising at least a 2291 nucleotide long stretch which corresponds to the nucleic acid sequence of SEQ ID NO:1.

29. The nucleic acid molecule of claim 24, further defined as comprising a nucleic acid fragment of up to 1,000 basepairs in length.

30. The nucleic acid molecule of claim 24, further defined as comprising a nucleic acid fragment of up to 500 basepairs in length.

31. The nucleic acid molecule of claim 24, further defined as comprising a nucleic acid fragment of up to 100 basepairs in length.

32. The nucleic acid molecule of claim 24, further defined as comprising a nucleic acid fragment of up to 50 basepairs in length.

33. A method of expressing a DNA molecule encoding a p48 polypeptide having the amino acid sequence of SEQ ID NO:2 or a p46 polypeptide having the amino acid sequence of SEQ ID NO:10, comprising the steps of:
   (a) preparing a recombinant vector in which said DNA molecule is postioned under the control of a promoter;
   (b) intoducing said recombinant vector into a host cell;
   (c) culturig said host cell under conditions effective to allow expression of the encoded p48 or p46 polypeptide; and
   (d) collectin said expressed p48 or p46 polypeptide.

34. The method of claim 33, wherein said recombinant vector is a plasmid.

35. The method of claim 33, wherein said host cell is a yeast cell.

36. A method of producing a recombinant p48 polypeptide having the amino acid seguence of SEQ ID NO:2 or a p46 polypeptide having the amino acid sequence of SEQ ID NO:10, comprising culturing yeast cells capable of expressing recombinant p48 or p46 under conditions effective to obtain a p48 or p46 polypeptide, and collecting said recombinant p48 or p46 polyptide.

37. An isolated nucleic acid molecule which comprises at least a 30 nucleotide long sttetch which corresponds to the nucleic acid sequence of SEQ ID NO:9.

38. The nucleic acid molecule of claim 37, further defined as comprising at least a 50 nucleotide long stretch which corresponds to the nucleic acid sequence of SEQ ID NO:9.

39. The nucleic acid molecule of claim 38, further defined as comprising at least a 100 nucleotide long stetch which corresponds to the nucleic acid sequence of SEQ ID NO:9.

40. The nucleic acid molecule of claim 39, further defined as comprising at least a 1000 nucleotide long stetch which corresponds to the nucleic acid sequence of SEQ ID NO:9.

41. The nucleic acid molecule of claim 40, further defined as comprising at least a 1992 nucleotide long stretch which corresponds to the nucleic acid sequence of SEQ ID NO:9.

42. The nucleic acid molecule of claim 37, further defined as comprising a nucleic acid fragment of up to 1,000 basepairs in length.

43. The nucleic acid molecule of claim 37, further defined as comprising a nucleic acid fragment of up to 500 basepairs in length.

44. The nucleic acid molecule of claim 37, further defined as comprising a nucleic acid fragment of up to 100 basepairs in length.

* * * * *

UNITED STATES PATENT AND TRADEMARK OFFICE
CERTIFICATE OF CORRECTION

PATENT NO.    : 6,071,715
DATED         : June 6, 2000
INVENTOR(S)   : Yue-Wei Qian and Eva Y.H.P. Lee It is certified that error appears in the above-identified patent and that said Letters Patent is hereby corrected as shown below:

Column 40,
Line 43, please add -- host -- before the first instance of "cell".

Column 41,
Line 27, please delete "culturig" and insert therefor -- culturing --.
Line 30, please delete "collectin" and insert therefor -- collecting --.

Column 42,
Line 2, please delete "seguence" and insert therefor -- sequence --.
Line 7, please delete "polyptide" and insert therefor -- polypeptide --.
Line 9, please delete "sttetch" and insert therefor -- stretch --.
Line 16, please delete "stetch" and insert therefor -- stretch --.
Line 19, please delete "stetch" and insert therefor -- stretch --.
Line 22, please delete "1992" and insert therefor -- 1929 --.

Signed and Sealed this

Fifteenth Day of January, 2002

Attest:

Attesting Officer

JAMES E. ROGAN
Director of the United States Patent and Trademark Office